United States Patent [19]

Kahn et al.

[11] 4,441,357

[45] Apr. 10, 1984

[54] PRESSURE MONITORING AND LEAK DETECTION METHOD AND APPARATUS

[75] Inventors: Alan R. Kahn, Madison; Kenneth R. Clark, Cottage Grove; Dennis E. Bahr, Middleton, all of Wis.

[73] Assignee: Meadox Instruments, Inc., Oakland, N.J.

[21] Appl. No.: 354,610

[22] Filed: Mar. 4, 1982

[51] Int. Cl.³ .......................... G01N 3/02; A61B 5/00
[52] U.S. Cl. .......................................... 73/40; 128/748
[58] Field of Search .................. 128/748, 672–675; 73/40, 40.5 R, 49, 49.1, 49.2, 49.5

[56] References Cited

U.S. PATENT DOCUMENTS

| | | |
|---|---|---|
| 2,831,478 | 4/1958 | Uddenberg et al. |
| 2,936,611 | 5/1960 | Le Mat et al. ............... 73/40 |
| 3,099,268 | 7/1963 | Bigliano . |
| 3,299,882 | 1/1967 | Masino . |
| 3,818,765 | 6/1974 | Eriksen . |
| 3,831,588 | 8/1974 | Rindner . |
| 3,921,436 | 11/1975 | Plegat ..................... 73/40 |
| 4,003,141 | 1/1977 | Le Roy . |
| 4,059,984 | 11/1977 | Uhlarik . |
| 4,128,013 | 12/1978 | Perry . |
| 4,147,161 | 4/1979 | Ikebe et al. |
| 4,167,868 | 9/1979 | Bobo et al. ............... 73/49.5 |
| 4,206,761 | 6/1980 | Cosman . |
| 4,206,762 | 6/1980 | Cosman . |
| 4,393,878 | 7/1983 | Kahn . |

OTHER PUBLICATIONS

Levin, A. B., "The Use of a Fiberoptic Intracranial Pressure Monitor in Clinical Practice", Neurosurgery, vol. 1, No. 3, Nov./Dec. 1977, pp. 266–271.

Brochure by Ladd Research Industries, Inc., "Intracranial Pressure Monitor for Continuous Measurement of ICP."

Primary Examiner—William E. Kamm
Assistant Examiner—Francis J. Jaworski
Attorney, Agent, or Firm—Isaksen, Lathrop, Esch, Hart & Clark

[57] ABSTRACT

A closed pressure monitoring system (20) is disclosed in which a pump (27) delivers gas on a supply line (22, 29) through a first accumulator chamber (30) to a load device (21) and returns the gas on a return line (23, 28) through a second accumulator chamber (34) to the pump (27). After pressures in the first and second chambers stabilize, the pressures are compared, and a leak warning signal is given if the compared pressures changed with respect to one another over time. The system is particularly adapted to use a pressure sensor as the load (21) which is implanted within a human patient. The pressure sensor receives air from a restrictor (32) in the supply line (22, 29) and is operative to maintain the pressure in the supply line substantially equal to the pressure surrounding the sensor.

23 Claims, 22 Drawing Figures

Microfiche Appendix Included
(2 Microfiche, 68 Pages)

PRESSURE MONITORING AND LEAK DETECTION METHOD AND APPARATUS

This application includes a microfiche appendix listing of a computer program having 68 frames.

TECHNICAL FIELD

This invention pertains generally to the field of pressure sensors and monitoring equipment and particularly to physiological sensing equipment wherein a sensor is implanted within the body of a patient to monitor internal pressures.

BACKGROUND ART

As an aid in the diagnosis and treatment of disease, it is often desirable to monitor the pressures at various positions within a patient's body or adjacent internal organs. A particular example is the measurement of the intracranial pressure within a patient's skull, since such measurements provide an indication of abnormalities in perfusion pressure or fluid retention, and allow the effect of drugs on intracranial pressure to be accurately monitored for effective treatment.

Various types of sensors are now utilized to measure internal body pressures, including electrical pressure transducers which transmit an elctrical signal indicative of the pressure through transmission wires out of the patient to a recording device, and pressure sensing heads which expand or contract in response to the pressure within the patient and communicate through a tube from the patient to a remote transducer which converts the pressure within the tube to a signal which can be displayed to the operator. The use of an electrical transducer implanted within a patient carries the obvious risks of shocks and short circuits, as well as the noise and baseline drift problems associated with any electrical transducer of a size small enough to be implanted. Direct pressure transmitting systems suffer from a lack of accuracy because of the distance that the pressure head must be transmitted from the patient to the remote transducer. The connection of the implanted sensing head through a tube to an external transducer also presents the possibility of a rupture or leak which would release air into the patient and possibly provide a source of infection.

In another type of pressure sensing apparatus, air flow is directed to a pressure sensor which includes a diaphragm covering a cavity within the sensor body. The diaphragm meters flow through an orifice by restricting or closing the orifice; the flow of air through the sensor is thereby controlled to equalize the pressure on both sides of the diaphragm, allowing the pressure at the sensor to be accurately read by reading the pressure of the air flowing in the tube leading to the sensor. In such a system, as well as in those which use a pressure sensing head which transmits the pressure through a tube to an external transducer, there is a small but definite risk that air (or other gas being used as the transmission medium) may leak from either the tubes or the sensor into enclosed spaces within the patient. Even leaks which occur outside the patient are detrimental to accurate measurement of the pressures within the patient.

Any closed, gas circulating system, in addition to those described above for physiological monitoring, may be subject to leakage which can effect system performance. A leak within such closed systems can result in abnormal pressures within the apparatus and erroneous data.

DISCLOSURE OF THE INVENTION

The apparatus of the present invention is particularly suited to monitoring pressures sensed by a pressure sensor which has been implanted within a human subject, allowing very accurate pressure readings to be obtained with a high degree of safety. The pressure sensor utilized is preferably of the type which has a diaphragm covering a cavity within the sensor body and positioned to open and close an orifice within the cavity. A substantially constant air flow is provided to the cavity with air being withdrawn through the orifice when it is uncovered by the diaphragm. The metering of the orifice by the diaphragm maintains the pressure in the cavity substantially equal to the pressure on the outside of the diaphragm. The system of the invention which supplies air flow to the sensor and returns air from the sensor is completely closed and sealed. Air is circulated by a pump which directs it through tubing to a first accumulator chamber and thence through a restrictor to the sensor, and the air is returned from the sensor through tubing to a second accumulator chamber and thence back to the inlet of the pump. All of these structures are sealed so that air cannot leak out of the system and potentially contaminated outside air cannot be drawn in. The pressure within the tubing between the restrictor and the sensor is measured by a load pressure transducer; this measured pressure is substantially equal to the pressure within the cavity in the sensor, and the pressure in the cavity is itself substantially equal to the pressure outside the sensor.

Two two accumulator chambers allow the apparatus to measure both positive and negative pressures ambient to the pressure sensor. Preferably, the second accumulator chamber is larger than the first, and the system will stabilize such that the gauge pressure within the second chamber will be a negative pressure. The magnitude of this negative pressure will be equal to the positive pressure within the first chamber times the ratio of the volume of the first chamber to the volume of the second chamber. Since a negative or "vacuum" pressure is maintained within the second chamber, the pressure sensor, when sealed off from the atmosphere, can detect and allow measurement of negative pressures up to the magnitude of the negative pressure within the second accumulator chamber.

Since the flow rate through the first and second accumulator chambers must be equal if the system remains sealed, a difference in the flow rate through the two chambers indicates a leak into or out of the system, and the difference in flow rate will show up as a change in the relative pressures in the two chambers. Under steady state conditions, the ratio of pressures within the two chambers or the difference between the pressures in the two chambers must be a constant; therefore, a change in the ratio of pressures or the difference of the pressures indicates a leak condition. The pressures within these chambers are measured and automatically compared by a controller which provides a signal if the ratio or difference of pressures varies from a constant. A warning may be given to the operator that a leak has occurred. In addition, a bypass valve is preferably connected around the pump and is responsive to the leak signal to open and shunt the output of the pump back to its input. The pump may also be controlled to shut off in response to the leak signal. As the pump stops and the shunt valve opens, the pressures within the two accumulator chambers quickly equalize so that the flow of air to the sensor is cut off.

The utilization of the above described accumulator chambers in gas supply and return lines can also be advantageous in other closed gas flow systems where it is desirable to be able to detect leaks. Leaks can be detected in such systems by comparing the pressures in the two chambers in the manner described above.

For maximum accuracy and response time, the pressure measured in the line between the restrictor and the pressure sensor may be utilized to control the input power to the pump so as to vary the displacement and flow rate of the pump in direct relation to the measured sensor pressure. By so controlling the power to the pump, the flow rate through the sensor may be maintained substantially constant by compensating for the decreased flow rate normally occurring when the pressure at the sensor increases.

In addition, if the pressure within the first chamber is kept constant by controlling the pump, a system leak can be detected by monitoring only the pressure in the second chamber; this pressure will remain constant unless a leak occurs.

The monitoring of the pressure transducers, the comparison of the accumulator chamber pressures, and the control of the pump and pump bypass valve is preferably done by a microcomputer programmed to perform the monitoring and control tasks. The microcomputer controller is well adapted to display to an operator, in digital form or in a continuous read-out such as on a cathode ray tube or a strip chart recorder, the reading of the patient sensor pressure. The controller also preferably provides an audio warning signal to the operator if the patient pressure sensor transducer shows a pressure reading above or below selected upper and lower pressure limits. The controller is also well adapted to initialize the system and obtain the zero readings for all of the transducers and an initial reading for the pressure sensor in ambient air; thus, the operator of the equipment requires little training and the equipment does not need significant operator attention during the time that it is in use.

Further objects, features and advantages will be apparent from the following detailed description taken in conjunction with the accompanying drawings showing a preferred embodiment of apparatus for monitoring pressure and detecting leaks in accordance with the invention.

BEST MODE FOR CARRYING OUT THE INVENTION

Figure 1:
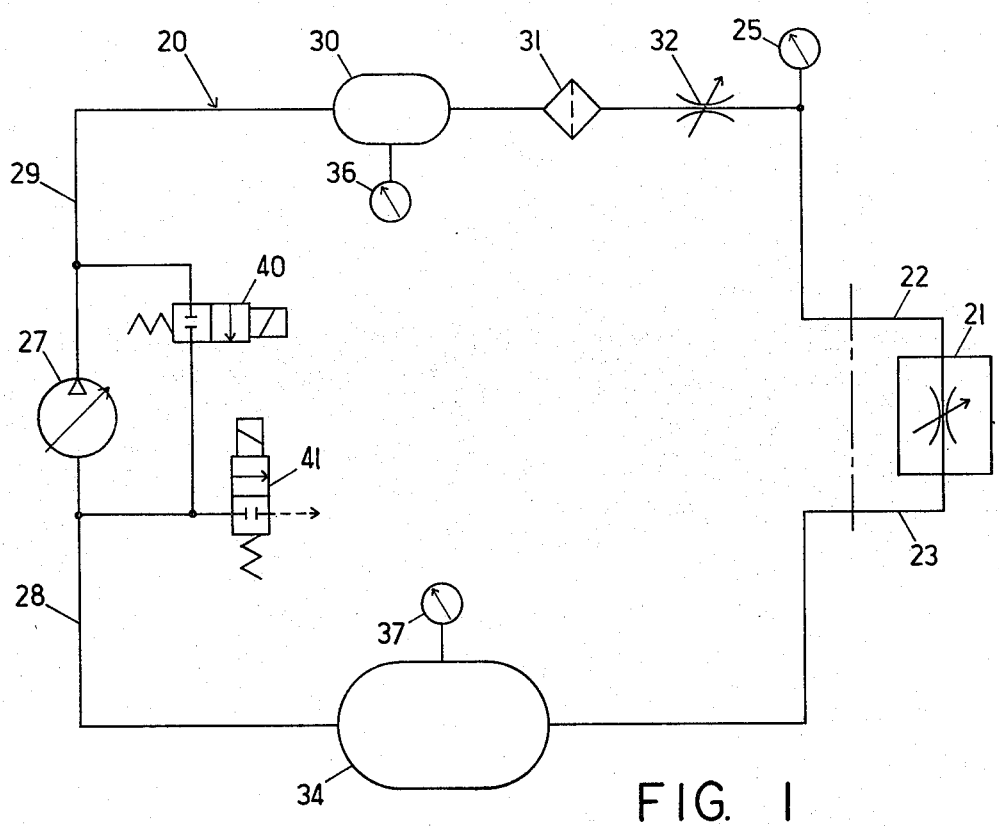
FIG. 1 is a schematic view of the apparatus of the invention.

With reference to the drawings, a schematic diagram of the air control components of the apparatus of the invention is shown generally at 20 in FIG. 1, and a variable impedance load to be monitored is shown at 21. For application in monitoring the pressures within a human patient, such as intracranial pressures, the load 21 would be a pressure sensor within the patient. A supply line 22 and a return line 23 extend from the sensor out of the patient's body to direct a stream of air, or other gas, to and from the sensor. The construction of a preferred pressure sensor adapted for use in the present apparatus is described in greater detail below. Generally the preferred pressure sensor 21 responds to changes in pressure within the patient by restricting or closing off the flow of gas from the line 22 when the patient pressure increases, and opening to reduce the impedance to the flow of gas in the line 22 when the pressure within the patient decreases. The flow rate within the line 22 is preferably maintained substantially constant, so that the increase or decrease in the impedance to the flow by the sensor 21 is reflected in an increase or decrease in the pressure within the line 22, which is monitored by a load pressure transducer 25. When an equilibrium is reached, the pressure within the supply line 22, which is read by the load transducer 25, will be substantially equal to the pressure outside the sensor 21.

The source of the flow of gas (for example, air) is a pump 27 which draws air in at an inlet from a return line 28 and forces it out at an outlet on a supply line 29. The air flow from the line 29 passes into a first accumulator chamber 30 and then out of the chamber on the supply line 22 through a bacteriological filter 31 and a flow restrictor 32 and thence to the flow sensor 21. The flow of air is delivered back from the sensor through the return line 23 to a second accumulator chamber 34 which is connected to the return line 28 to return the flow of air to the pump. The pressure within the first chamber 30 is monitored by a first pressure transducer 36 and the pressure within the second chamber 34 is monitored by a second transducer 37.

A normally closed solenoid operated bypass valve 40 is connected to the lines 28 and 29 to selectively shunt the flow out of the pump 27 back to its inlet, while a solenoid operated pressure release valve 41 is connected to the line 28 to selectively vent the line 28 to ambient air.

Prior to the start-up of operation, the valves 40 and 41 are opened to allow all of the components within the system, such as the chambers 30 and 34 and the interconnected supply and return lines, etc., to reach ambient pressure. The valves 40 and 41 are then closed and the pump 27 is started.

It is clear from an examination of FIG. 1 that the flow rate in the lines 28 and 29 must always be equal, and that the flow rate in the lines 22 and 23 must also always be equal. However, during an initial period of time after the pump 27 is started, the flow rate in the lines 28 and 29 is not necessarily equal to the flow rate in the lines 22 and 23. This is true because air accumulates for a period of time within the chamber 30 to pressurize this chamber above ambient, while air is withdrawn from the chamber 34 to reduce the pressure within this chamber below ambient. Eventually, the system reaches a steady state in which the pressures within the chambers 30 and 34 do not substantially change, and the flow rate within the lines 28 and 29 then equals the flow rate within the lines 22 and 23. If the air within the system is assumed to act as an ideal gas, the relationship between the pressures in the two chambers can be simply expressed. Letting the steady state pressure within the chamber 30 be denoted as $P_1$ while the volume of the chamber is denoted as $V_1$, and letting the steady state pressure within the chamber 34 be denoted as $P_2$ and the volume of the chamber be denoted as $V_2$, the relationship between the pressure in chamber 30 and the pressure in chamber 34 will be:

$$P_2 = -P_1(V_1/V_2) \text{ or } P_2/P_1 = -V_1/V_2$$

The volume of the chamber 34 is preferably made larger than that of the chamber 30 by some integer ratio. For example, if the volume of the chamber 34 is 10 times the volume of the chamber 30, then the following relationship will exist between the pressures that are read by the transducers 36 and 37:

$$P_2 = -P_1/10$$

or $$10P_2 + P_1 = 0$$

The foregoing equations will hold true if there are no leaks of air into or out of the system; the equations will not hold true if there are such leaks. For example, if air should escape from the line 22, the pressure in the chamber 30 will not change significantly, but the pressure in chamber 34 will drop because less air is flowing in through the line 23 than is being withdrawn through the line 28. If a leak develops in the line 23, and air is drawn into the line, the pressure within the chamber 34 will increase because more air is entering the chamber 34 from the line 23 than is being withdrawn from the line 28. Similar changes in the pressure within one or the other of the chambers 30 and 34 will occur if any of the lines are blocked.

By comparing the pressures in the chambers 30 and 34, it is possible to determine whether a leak has occurred. For example, the quotient of the pressures should be equal to the inverse of the quotient of the respective chamber volumes, a constant. If the quotient of the pressures changes over time, a leak must exist. Alternatively, the comparison can be made by adding 10 times the gauge pressure in the chamber 34 plus the gauge pressure within the chamber 30, and comparing the absolute value of the sum with some small constant; a leak or block is determined to have occurred if the absolute value of the sum is greater than the constant. For maximum accuracy, the effective volumes of the supply and return lines must be included when determining $V_1$ and $V_2$.

The vacuum that is maintained within the larger chamber 34 also is a particular advantage if the sensor 21 develops a leak since the chamber 34 will exert a vacuum draw on the sensor 21 which will tend to initially draw in gas or liquid from around the sensor.

The sensing of pressure within the chambers 30 and 34 by the transducers 36 and 37 can be used by a controller responsive to signals from the transducers to determine when a leak occurs; the controller may then translate this determination into the action of turning off the pump 27 and opening up the solenoid valve 40 as well as warning an operator. The chamber 30, although under pressure, is isolated from the sensor 21 by the restrictor 32, and thus will exhaust its air through the valve 40 to the low pressure chamber 34 when the valve 40 is opened. The chamber 34, however, is directly connected to the sensor through a low impedance line and thus will tend to exert a vacuum draw on the sensor even as the valve 40 is opened, thereby tending to withdraw air from the sensor rather than allowing the sensor to receive air under pressure which might otherwise be injected to an area outside the sensor.

The negative pressure maintained within the chamber 34 also allows the sensor 21 to respond to pressures lower than ambient air pressure. As is apparent from FIG. 1, if the sensor 21 opens up when exposed to negative pressure so that it provides little or no impedance to the air flow, the pressure read by the transducer 25 will approach the pressure in the chamber 34, which is thus the lower limit of pressures that can be monitored by the sensor 21.

The pump 27 preferably operates at an inlet to outlet pressure differential of about 10 to 14 psig while the pressure in the chamber 30 is maintained at about 10 psig. If the volume of the chamber 34 is ten times that of the chamber 30, the pressure in the chamber 34 will theoretically be about −1 psig. However, because of the volume of the supply and return lines, the chamber 34, in actual practice, will be at a somewhat lower pressure. The pressure within the line 22, as read by the transducer 25, will generally be in the range of −1 to +3 psig (−50 to +150 mm Hg). Because the pressure within the chamber 30 is substantially greater than the pressure within the line 22 as a result of the pressure drop across the restriction 32, which is preferably an adjustable orifice to allow the pressure drop to be varied, the flow through the line 22 will be substantially constant despite the variations in resistance to flow caused by the sensor 21 as it responds to ambient pressure. It is noted, however, that the flow sensor 21 is initially calibrated by operating it in ambient air and defining the value read by the transducer 25 as zero pressure. For maximum accuracy, it is preferred that the flow rate which obtains during the initial calibration of the flow sensor be maintained during measurement of the changes in pressure when the flow sensor 21 is placed in a patient. Because the flow rate through the sensor tends to decrease as the pressure within the line 22 increases, as read by the transducer 25, if the pump 17 has a controllable variable displacement it can be controlled by the signal from the transducer 25 to compensate by increasing its output pressure to maintain a substantially constant flow rate.

Figure 2:
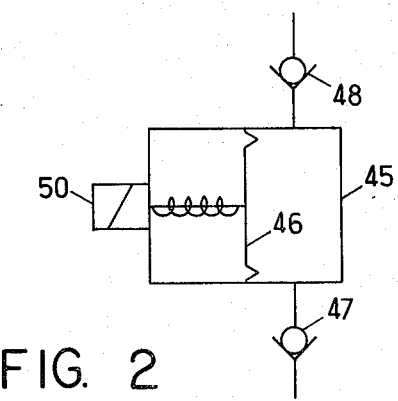
FIG. 2 is a schematic view of one embodiment of a pump which can be utilized in the apparatus of the invention.

One type of pump which has been found particularly suited to this application is a WISA bellows pump, a simplified schematic of which is shown in FIG. 2. As the bellows 46 within the pump body 45 moves in and out, air is drawn in through an inlet check valve 47 and is forced out through an outlet check valve 48. The bellows diaphragm 46 is moved outwardly by a solenoid 50 and springs back inwardly to draw in air when the solenoid 50 is de-energized. The solenoid 50 is typically driven by 60 Hz line voltage which is passed through a diode so that the solenoid is energized and de-energized 60 times a second to drive the bellows diaphragm 46 at a similar rate. The displacement of the pump can be simply adjusted by adjusting the height of the voltage pulses provided to the solenoid. It is also apparent that other pumps which are responsive to a control signal to control the displacement or flow rate through the pump can also be utilized for this application.

Figure 3:
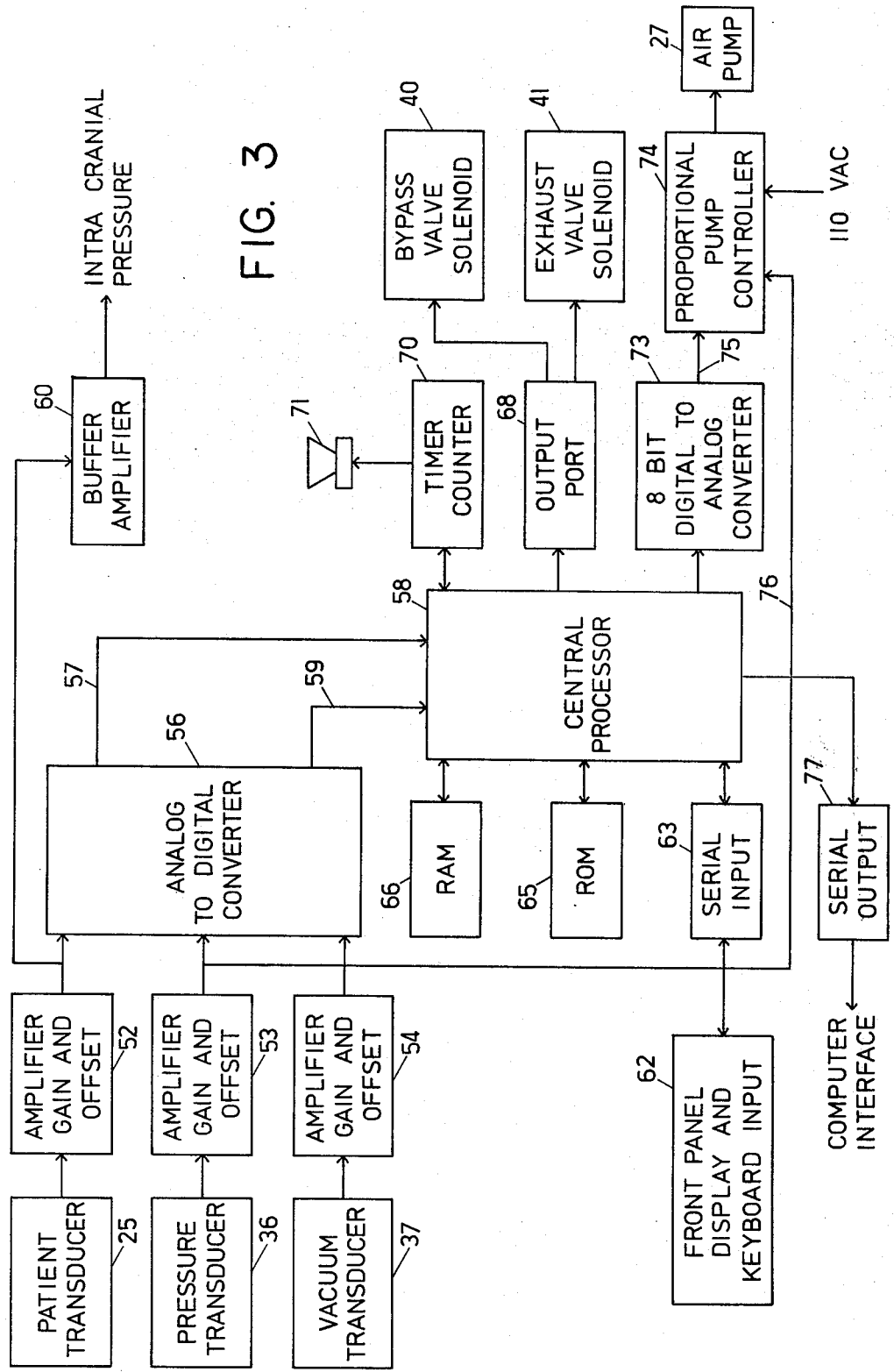
FIG. 3 is a block diagram showing the controller portion of the apparatus.

The electronic control means components of the apparatus are shown in a schematic block diagram view in FIG. 3. The outputs of the patient transducer 25, the pressure transducer 36, and the vacuum transducer 37 are fed, respectively, to amplifier units 52, 53, and 54, which provide impedance isolation, variable gain, and variable offsets. The outputs from the amplifiers 52, 53 and 54 are provided to an analog to digital converter 56 which directs an 8 bit output on a line 57 to a microprocessor 58. The microprocessor, or CPU, 58 controls the A to D converter 56 through select lines 59 so as to receive data from a desired one of the transducers 25, 36 or 37. The analog output of the patient transducer 25, after passing through the amplifier unit 52, is fed through a buffer amplifier 60 and is available to an analog read out device such as a strip chart recorder of a CRT display.

Data is provided to the central processor 58 from a front panel display and keyboard unit 62 through a two-way serial converter 63. As explained further below, the data input from the keyboard may be commands to start up the system, to calibrate the various transducers, to set warning indicator limits to be used to warn of excessive over or under pressures read by the patient transducer, and for other purposes. The front panel display provides the user an indication of the pressure read by the patient transducer, preferably in base 10 digital readout, and also provides communication to the user during the various data input and status checking operations.

The system program is contained in a ROM unit 65 connected on a data bus to the CPU 58, and data storage is provided in a RAM unit 66 connected through a data bus to the CPU 58. The CPU sends a signal through an output port 68 to the bypass valve solenoid 40 and the exhaust valve solenoid 41 at the proper time to open these valves during initialization of the system, and will send a signal to open the valve 40 if a leak condition is noted as a result of monitoring the pressure transducer 36 and the vacuum transducer 37. As explained futher below, the CPU 58 also provides an output signal through a timer/counter 70 and thence to a audio speaker 71 to provide a warning to the operator whenever the pressure read by the patient/load pressure transducer 25, and interpreted by the CPU 58, exceeds a preprogramed over- or under-pressure limit.

As indicated above, it is desirable to maintain the flow rate through the patient transducer at as constant a rate as possible, and this can be accomplished by varying the displacement of the air pump 27 in direct relationship to the pressure level read by the patient transducer. To accomplish this, the CPU 58 processes the patient transducer signal and provides an output to a digital to analog converter 73 which provides an analog signal on a line 75 to a proportional pump controller 74. The pump controller, which also receives an analog signal from the pressure transducer 36 on a line 76, modulates the magnitude of the AC signal provided to the pump 27.

To allow interconnection to other data processing equipment, the CPU 58 also provides an output signal indicating the level of the patient transducer to a parallel to serial converter unit 77. This signal may then be interfaced with other data processing equipment for recording and subsequent processing, or for real time processing.

Figure 4:
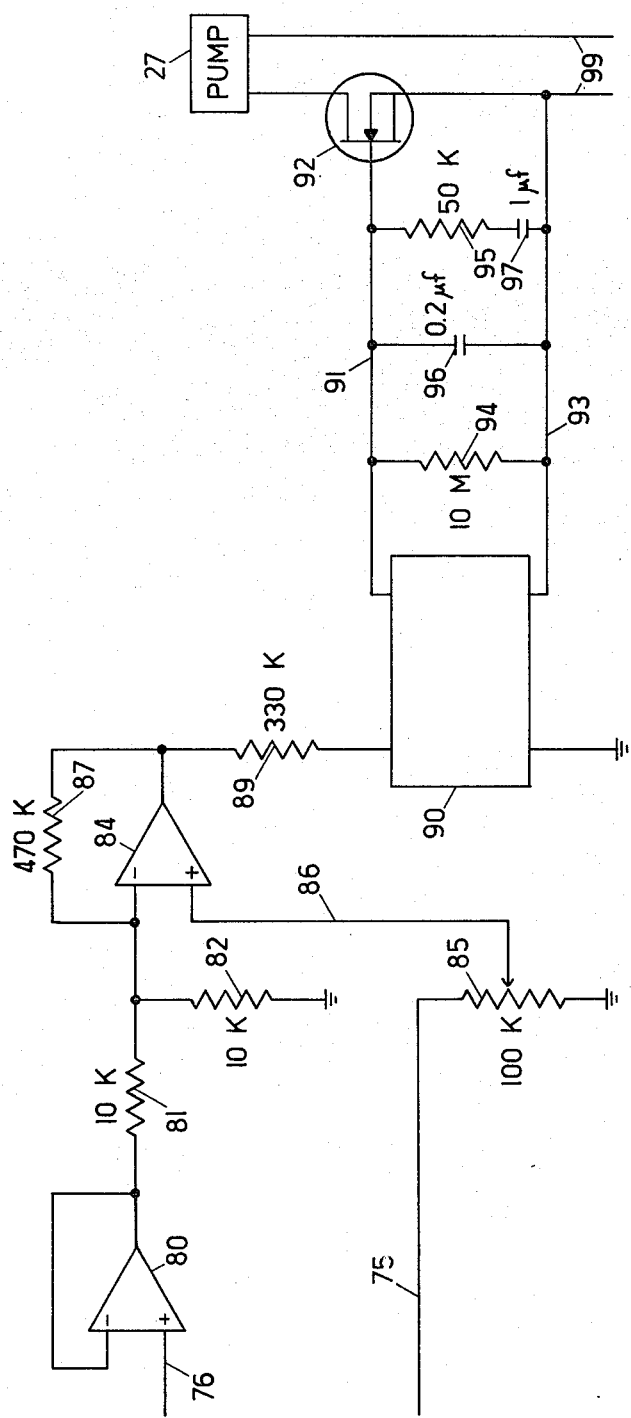
FIG. 4 is a schematic circuit diagram of the proportional pump driver.

A schematic diagram of the proportional pump controller 74 is shown in FIG. 4. The signal indicative of the reading of the pressure transducer 36 is passed on the line 76 through a buffer amplifier 80 and thence through a voltage divider composed of resistors 81 and 82, with the resulting voltage applied to the negative input of an operational amplifier 84. The analog output signal of the D to A converter 73 is applied from the line 75 through a potentiometer 85; the voltage taken off of the wiper of the potentiometer is transmitted on a line 86 to the positive input of the amplifier 84. A feedback resistor 87 connects the output of the amplifier 84 to its negative input. In this manner the signal from the pressure transducer 36, indicating the pressure within the chamber 23, is subtracted from the signal received from the digital to analog converter 73, a signal proportional to the pressure read by the patient transducer 25. The amplifier output is thus related to the difference in pressure between the transducers 36 and 25, which difference is proportional to the flow rate through the restrictor 32. The output of the amplifier 84 passes through a series resistor 89 to a opto-isolater 90 which isolates the control portions of the circuitry from AC power. One terminal of the opto-isolater 90 is connected by a conducting line 91 to the gate of a field effect transistor 92 and the other terminal of the opto-isolater 90 is connected by a conducting line 93 to the source terminal of the FET 92. Resistors 94 and 95 and capacitors 96 and 97 are connected across the lines 91 and 93 to filter the output of the opto-isolater. One of a pair of AC power lines 99 is connected to the source terminal of the FET, while the drain terminal of the FET extends to the pump 27, as does the other AC power line. As noted above, the pump is preferably a solenoid driven diaphragm-bellows pump which receives half-wave AC power. The output of the opto-isolater 90 modulates the height of the pulses delivered through the FET 92 to the pump so that the pulses vary in magnitude in proportion to the output of the amplifier 84. The normal or steady state pulse magnitude is selected to be sufficient to maintain a desired pressure level within the chamber 30 under initial or normal air flow conditions within the system. It is apparent from examination of the system that an increase in the pressure sensed by the transducer 25 results in an increase in the magnitude of the pulses provided to the pump and therefore greater displacement of the pump diaphragm on every stroke, thereby tending to increase the pressure within the air chamber 30. As the pressure within the chamber 30 increases, the magnitude of the pulses provided to the pump decreases toward the normal magnitude; with proper adjustment of the system parameters, when the steady state is reached, the chamber 30 will be at a higher pressure sufficient to provide the desired constant flow through the restrictor 32 despite the higher pressure observed at the pressure transducer 25. Conversely, if the pressure transducer 25 senses a drop in pressure, the output of the amplifier 84 will decrease from the normal offset voltge level, thereby causing the FET 92 to decrease the magnitude of the pulses provided to the pump 45 below the normal magnitude. The displacement of the diaphragm with each pulse will therefore be less than under normal conditions, allowing the air chamber 30 to bleed down in pressure through the restrictor 32 until it reaches a new lower level sufficient to maintain the desired flow rates through the restrictor.

It will be apparent to those skilled in the art that the control components shown in FIG. 3 are of standard design and the interconnections therebetween are readily apparent. As an example of commercial units satisfactory for implementing the controller of the present invention, the CPU 58 may comprise a Mostek MDX-CPU2, a Z80 based microprocessor, the I/O Serial input and output devices 63 and 77 may be Mostek MDX-SIO units, and the analog to digital converter 56 may be a Mostek MDX-AIO, compatible with the CPU unit. The RAM 66, compatible with the aforementioned CPU, is preferably a 4K memory with an 8 bit word, while the ROM 65 may contain the system program within a 6K memory utilizing an 8 bit word. A display panel of the type manufactured by Burr-Brown Research Corp. under the name TM177 has been found suitable, and is utilized in the programming for the apparatus described below. The pressure transducers 25, 36 and 37 may be proportional transducers such as those produced by Honeywell Microswitch. Such transducers are available to read from, for example, −5 psig to +5 psig, as appropriate for the load transducer 25, from 0 to −5 psig as appropriate for the vaccum transducer 37, and from 0 to 15 psig, as appropriate for the pressure transducer 36. The afore-mentioned Microswitch transducers provide an output signal varying from 1 to 6 volts about a null voltage midway in that range.

The above described control means of FIG. 3 is a preferred embodiment for carrying out the control functions of the system. It is quite apparent to those skilled in the art that there are other, equivalent embodiments for carrying out these control functions. For example, an analog signal circuit could easily be constructed to monitor the transducers 36 and 37 and provide a warning if a lead is detected. A simple circuit for doing so could include a summing amplifier which adds the output of the transducer 36 and ten times the output of the transducer 37, with the summing amplifier output then being compared in a comparator (or in two comparators, one for positive and one for negative outputs) with a small offset voltage, with a leak warning provided by the comparator if the offset is exceeded. The bypass valve solenoid may be operated by the output of such a comparator, and the pump 27 may be turned off by such a warning signal. It is also quite obvious that the pump may be controlled completely with analog circuitry by simply connecting the line 75 to the output of the amplifier 52. The other control and warning functions may also be embodied in analog circuitry. The comparison of the pressures within the chambers 30 and 34 may even be performed pneumatically, and a pneumatic pressure signal may be utilized to switch a bypass valve analogous to the valve 40.

Figure 5:
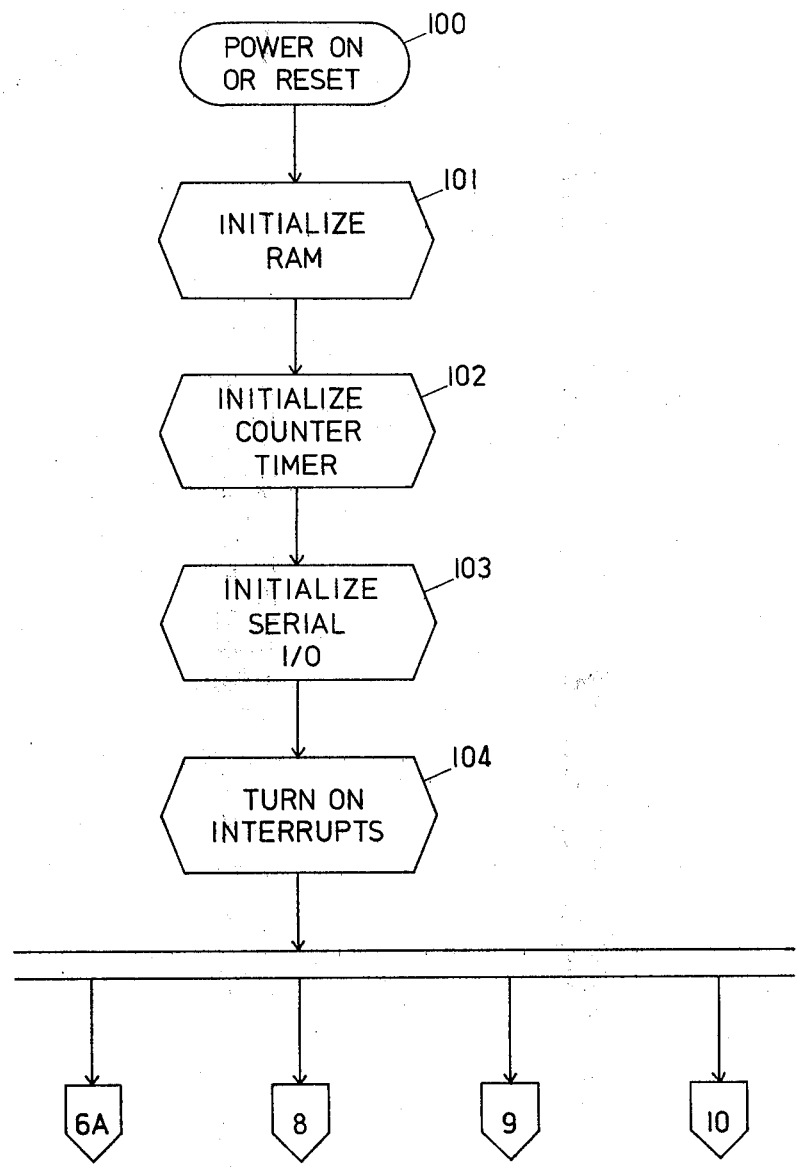
FIGS. 5–19 are flow charts which show the operating steps in the programming of the controller which carry out the monitoring and control tasks within the apparatus.

Flowcharts illustrating the operations of the program which monitors the data from the various transducers and controls the pump and solenoid valves are shown in FIGS. 5—19 and a program listing is set out in the microfiche appendix hereto. The program is designed to switch between various major tasks at interrupt times, with a scheduler program distributing control to one of the major tasks at each interrupt. For example, in the program that follows, an interrupt clock frequency of 125 times a second has been found satisfactory to allow adequate processing of data by each of the major tasks. As shown in FIG. 5, the activation of the power on switch by the operator (block 100) causes the computer to initialize the RAM memory (101), to initialize the counter/timer 70 (block 102), to initialize the serial input/output devices 63 and 77 (block 103), and to turn on the interrupts (block 104). The program, under the control of the scheduler, then distributes control at the sequential interrupt clock times to a command processor task, shown in FIGS. 6 and 7, a leak task shown in FIGS. 8A and 8B, a data acquisition task shown in FIG. 9, and a solenoid control task shown in FIG. 10. The connecting blocks shown in FIG. 5 at 6A, 8, 9 and 10 refer to the respective starting points on the flowchart shown in FIGS. 6, 8, 9, and 10, respectively. Similar connection block numbering is used throughout the flowchart. In addition to the major tasks which are controlled by the interrupts, several subroutines are accessed by the tasks and are shown in separate figures. Subroutines accessed by the command processor task are shown in FIGS. 11 and 12, subroutines accessed by the leak task are shown in FIGS. 13–18, and an analog to digital conversion subroutine which is accessed by the data acquisition task and communicates with the command processor task is shown in FIG. 19.

Figure 6:
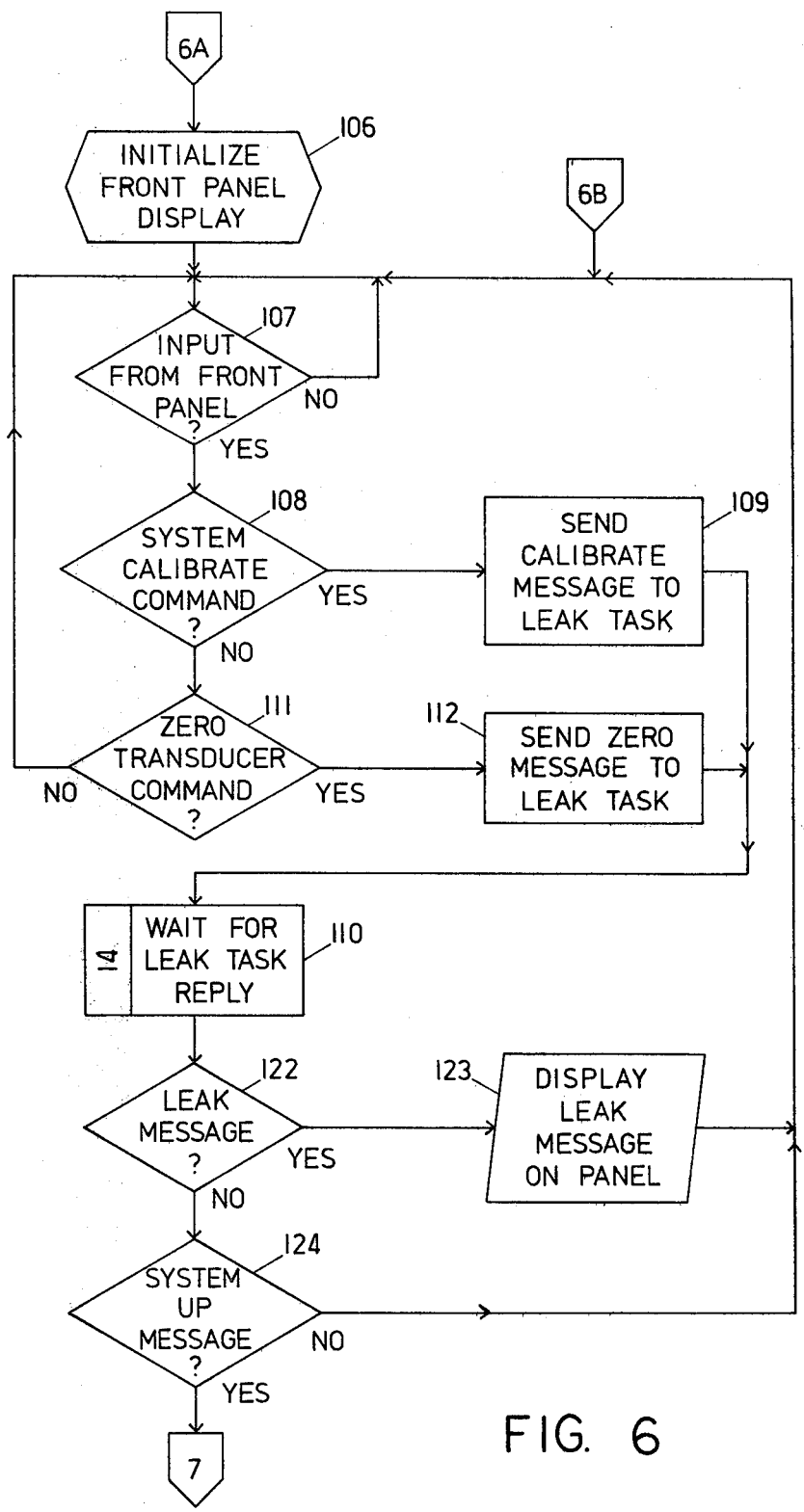
Figure 14:
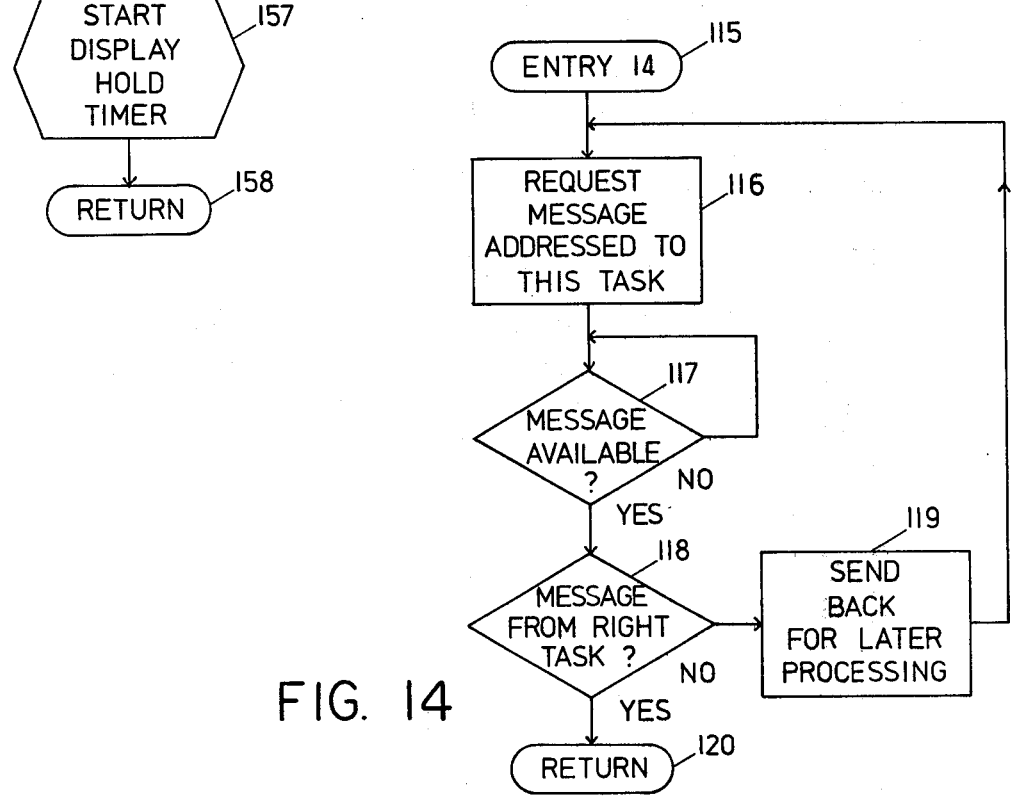

The command processor task shown in FIG. 6 begins with an initialization of the front panel display 62 (block 106). Thereafter, the program determines if there is input from the front panel (block 107). If not, the program recycles until input is received. If there is input from the front panel it is first determined if it is a system calibrate command (block 108); if so, a calibrate message is sent to the leak task (block 109) and the program proceeds to subroutine 14 (FIG. 14) to await a reply from the leak task (block 110). If the system calibrate command is not present, it is determined whether the command is a zero transducer command (block 111); if not, the program recycles to check for input from the front panel (block 107); if so, a zero message is sent to the leak task (block 112) and the program goes to subroutine 14 to await a reply from the leak task (block 110). Subroutine 14, shown in FIG. 14, is entered at block 115 and requests a message addressed to the task (block 116). If a message is not available, the program cycles until a message does become available (block 117); if the message is available it is determined whether the message is from the right task (block 118)—in this case from the leak task—and, if not, the message is sent back to the originating task for retention and later processing (block 119). If the message is from the right task, return is made to the main program (block 120). The message from the leak task will either be that there is a leak (a leak message) or that the system is up and operating satisfactorily (a system-up message). The command processor program shown in FIG. 6 first checks for the leak message (block 122) and if one is present, the leak message is displayed on the front panel (block 123) and the program returns to block 107 to check for further input from the front panel. If there is no leak message the program checks for a system up message (block 124); if none is available, the program returns to block 107 to check for input from the front panel. The lack of a system up message at this point would be indicative of the a failure of the system to properly calibrate during the performance of the leak task. If the system-up message is received, the program proceeds to the remainder of the command processor task, shown in FIG. 7.

The program proceeds to set a one second timer which controls the updating of the display at the front panel (block 126). The program then proceeds through loops in two branches depending on whether it is time to update the display (block 128). If not, the intracranial pressure is requested from the data acquisition task (block 129) and the program then proceeds to subroutine 11 (FIG. 11) which processes any available front panel input data (block 130).

Figure 11:
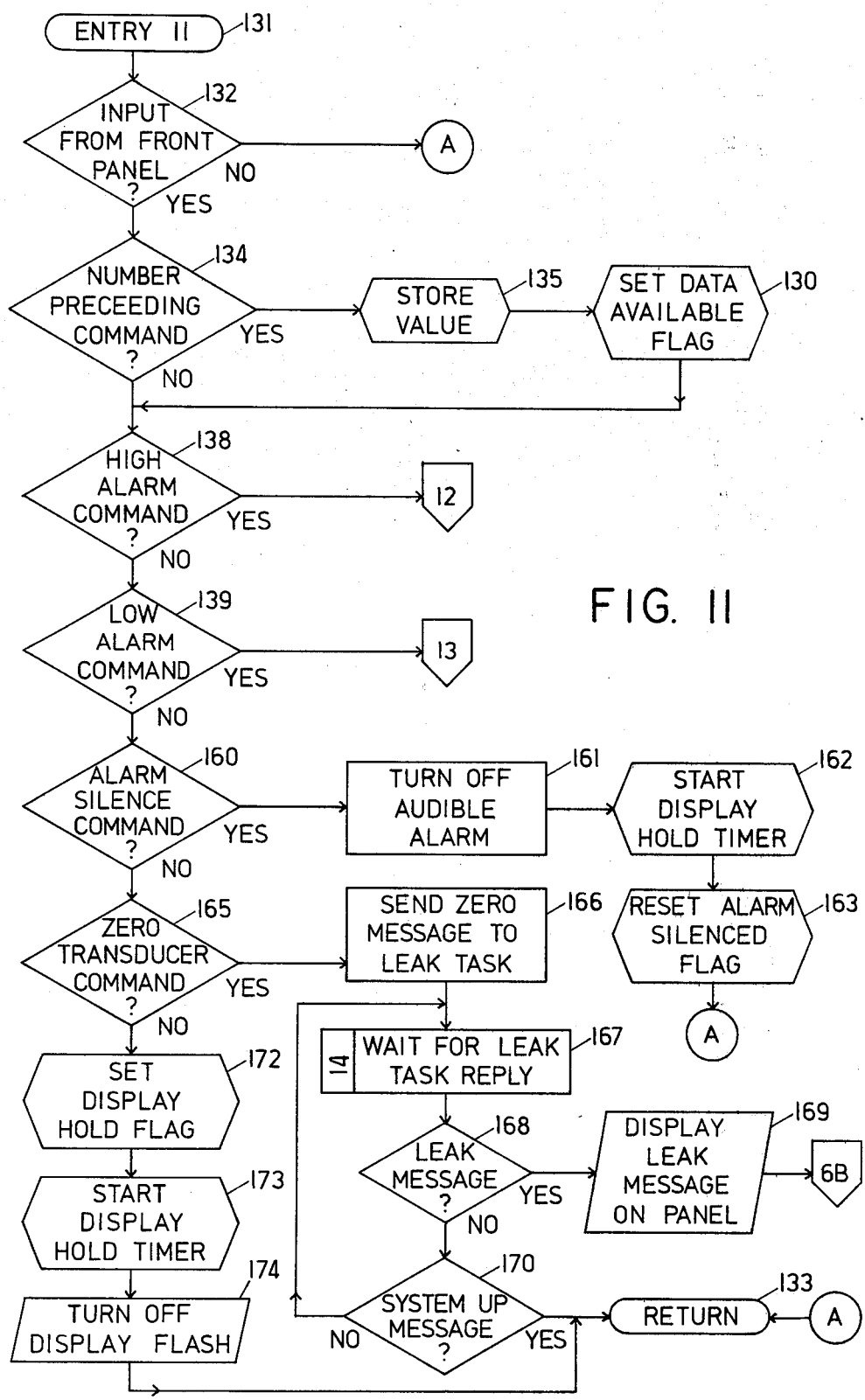
Figure 12:
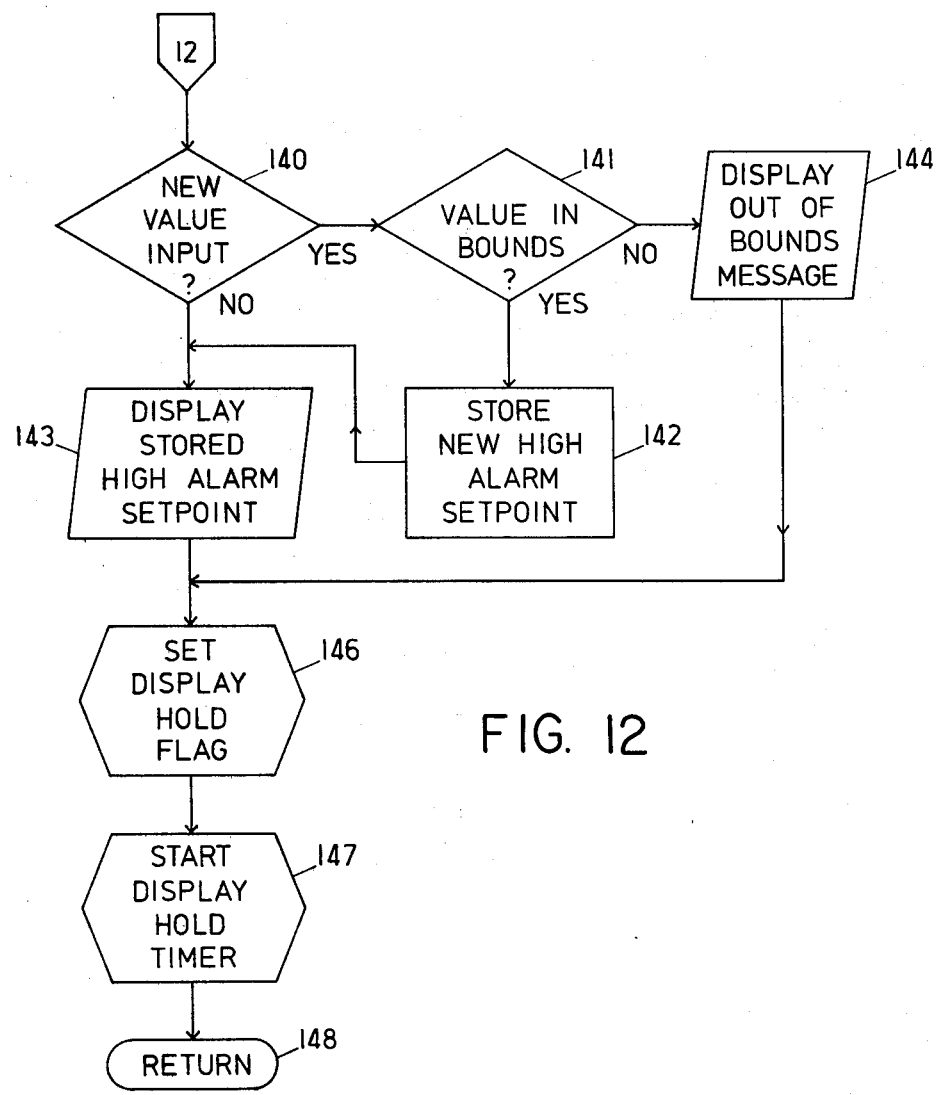

After entry into subroutine 11 (block 131), shown in FIG. 11, it is then determined whether there is input from the front panel (block 132); if not, the system returns to the main command processor program (block 133). If there is input from the front panel it is then determined if there is a number which preceeds the command (block 134), indicating that a high or low limit is being set, and if such a number is received, it is stored (block 135) and a data available flag is set (block 136). After the data available flag has been set, or if no number preceeds the command, it is then determined if there is a high alarm command (block 138) and, if so, the system proceeds to subroutine 12, shown in FIG. 12. If there is no high alarm command but there is a low alarm command (block 139), the system proceeds to subroutine 13 shown in FIG. 13.

Subroutine 12, FIG. 12, first determines if there is a new input value (block 140), and, if so, determines whether the value is within bounds (block 141), and, if so, stores the new high alarm set point (block 142) and then displays the stored high alarm set point (block 143). If there was no new input value, the program displays the previously stored high alarm set point. If the value is not in bounds (block 141), an out-of-bounds message is displayed on the front panel (block 144). After the high alarm set point is displayed and stored, or if the out-of-bounds message is displayed, the program proceeds to set a display hold flag (block 146), sets a display hold timer (block 147)—which holds the program for a few seconds to allow the operator to determine that the proper alarm value has been set—, and then returns to the main command processor program (block 148).

Figure 13:
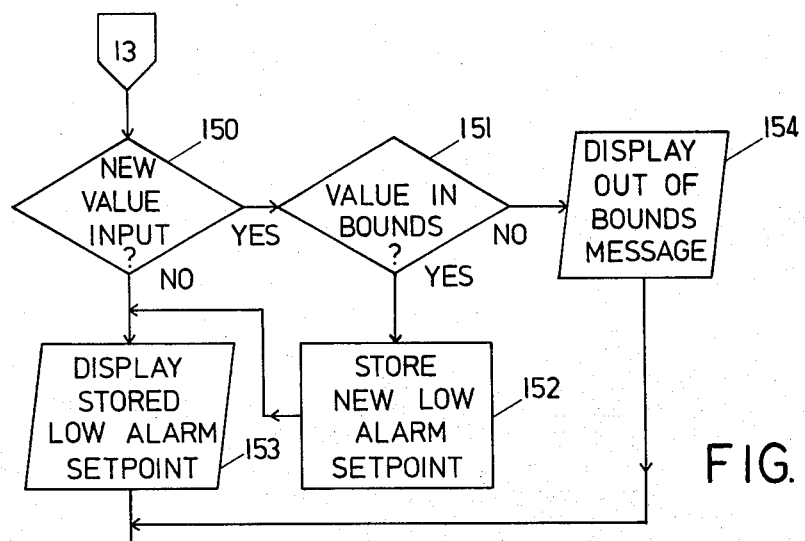

Subroutine 13, shown in FIG. 13, is accessed if a low alarm command is received, and first determines whether a new value input is received (block 150); if so, it determines if the value is in bounds (block 151), and if so, stores the new low alarm set point (block 152), and then displays the low alarm set point on the front panel (block 153). If the value is not in bounds, an out-of-bounds message is displayed (block 154). If no new value is received, the old value input is displayed (block 153). After display of the low alarm set point or display of the out-of-bounds message, a display hold flag is set (block 156), a display hold timer of several seconds is set (block 157), and the program returns (block 158) to the main command processor program at block 130.

If neither a high alarm command nor a low alarm command is received at blocks 138 and 139, subroutine 11, FIG. 11, then determines whether an alarm silence command has been received (block 160); if so, the audible alarm is turned off (block 161), a display hold timer of two seconds is started (block 162), the alarm silenced flag is reset (block 163), and the program returns (block 133) to the main command processor program at block 130.

If no alarm silence command was received, it is then determined whether a zero transducer command was received (block 165); if so, a zero message is sent to the leak task (block 166) and the system waits for the leak task reply (block 167), diverting into subroutine 14, FIG. 14, and then returning after the leak task has replied. It is then determined if there is a leak message (block 168), and, if so, the leak message is displayed on the front panel (block 169) and the program returns to the main command processor task at entry point 6B and awaits further instruction from the front panel at block 107. If there is no leak message, it is then determined if a system up message is available (block 170); if so, return (block 133) is made to the main command processor program at block 130. If the system up message is not received, the program diverts to subroutine 14 (block 167) to wait for a leak task reply having a valid message.

If a zero transducer command was not received at block 165, a display hold flag is set (block 172), a display hold timer is set (block 173), and the flashing of the display on the front panel is turned off (block 174) before the program returns (block 133) to the main command processor program at block 130. As explained below, the display of patient pressure is commanded to flash on and off if the intracranial pressure which has been read is greater than the program high limit or less than the program low limit. Input from the front panel which is neither a high alarm command, a low alarm command, an alarm silence command, or a zero transducer command, is read as a command to turn off the flashing of the display.

Figure 7:
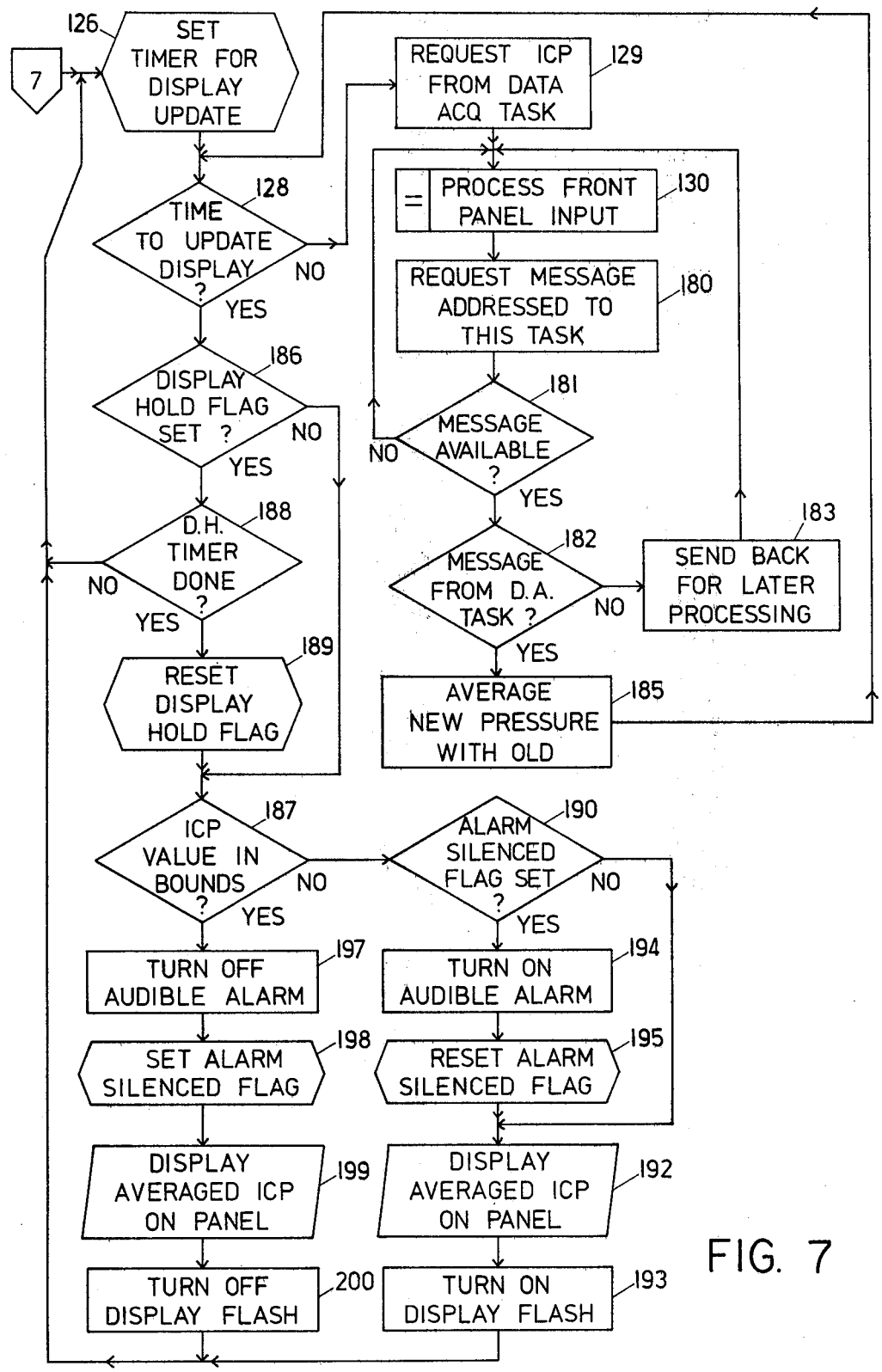

After completion of subroutine 11, at block 130, the command processor task, FIG. 7, sends a request for a message addressed to the task (block 180), and a check is made to see whether or not a message is availabe (block 181); if not, the program returns to subroutine 11, block 130, to process front panel input data. If a message is available, it is checked to see if it is from the data acquisition task (block 182); if not, the message is sent back to the task from which it is received to be processed later (block 183) and the program returns to block 130, subroutine 11, to process any new front panel input data. If a message is received from the data acquisition task it will be the patient pressure transducer data. Because the patient transducer will pick up transient readings of short duration, it is desirable to average out a few successive samples or sensor readings so as to provide a signal to the display at the time that the display is updated which is not affected by the transients. Satisfactory results can be obtained if the latest pressure reading sample is averaged with the next three immediately received pressure reading samples (block 185). The program then returns to block 128 and determines whether the timer at 126 has run and it is time to update the display. If not, the previously described cycle is repeated until it is time for display update, preferably at about one second intervals; the display hold flag is then checked to see if it is set (block 186) and, if not, the program proceeds to determine determine whether the intracranial pressure reading that has been obtained is within the bounds that have been previously programmed (block 187). If the display hold flag has been set, it is first determined whether the display hold timer is done (block 188), and, if not, program returns to block 126 and the timer for display update is reset. If the display hold has been released, or if the display hold timer had not been set, the program proceeds to reset the display hold flag (block 189) and determines if the intracranial pressure value found is in bounds (block 187). As indicated above, these limits will be set by the operator to provide an automatic indication of dangerous pressure levels; typically, normal intracranial pressure should be in the range of −25 mm to +150 mm of mercury, while a reading outside this range would be indicative of an abnormal or dangerous condition. If the pressure reading is not within these bounds, a check is made to see if the alarm silenced flag has been set (block 190) and, if not, the averaged intracranial pressure is displayed on the panel (block 192), the display flash is turned on (block 193), and the program returns to block 126 to set the timer for new display update. If the alarm silenced flag has not been set, the audible alarm is turned on (block 194) by sending a signal to the timer/counter 70 which drives the speaker 71 and the alarm silenced flag is reset (block 195) before the intracranial pressure reading is displayed (block 192) and the display flash is turned on (block 193).

If the intracranial pressure was found to be within bounds at block 187, the audible alarm is turned off (block 197), if it had been on, the alarm silenced flag is set (block 198) the averaged intracranial pressure is displayed on the front panel (block 199) and the flashing of the display is turned off (block 200), if the display had been flashing. The program then returns to set the timer for display update at block 126 and repeats the cycle.

It should be noted that the foregoing flow of the command processor task will be periodically interrupted and the other tasks, described below, will be performed in sequence. As noted from the description above, the command processor task, at various points in the program, sends messages to the other tasks and asks for messages from the other tasks. In turn, the other tasks will run and be interrupted at some point in the programming of the task, with each task being restarted at the point in the task program at which the interrupt occurred.

Figure 8A:
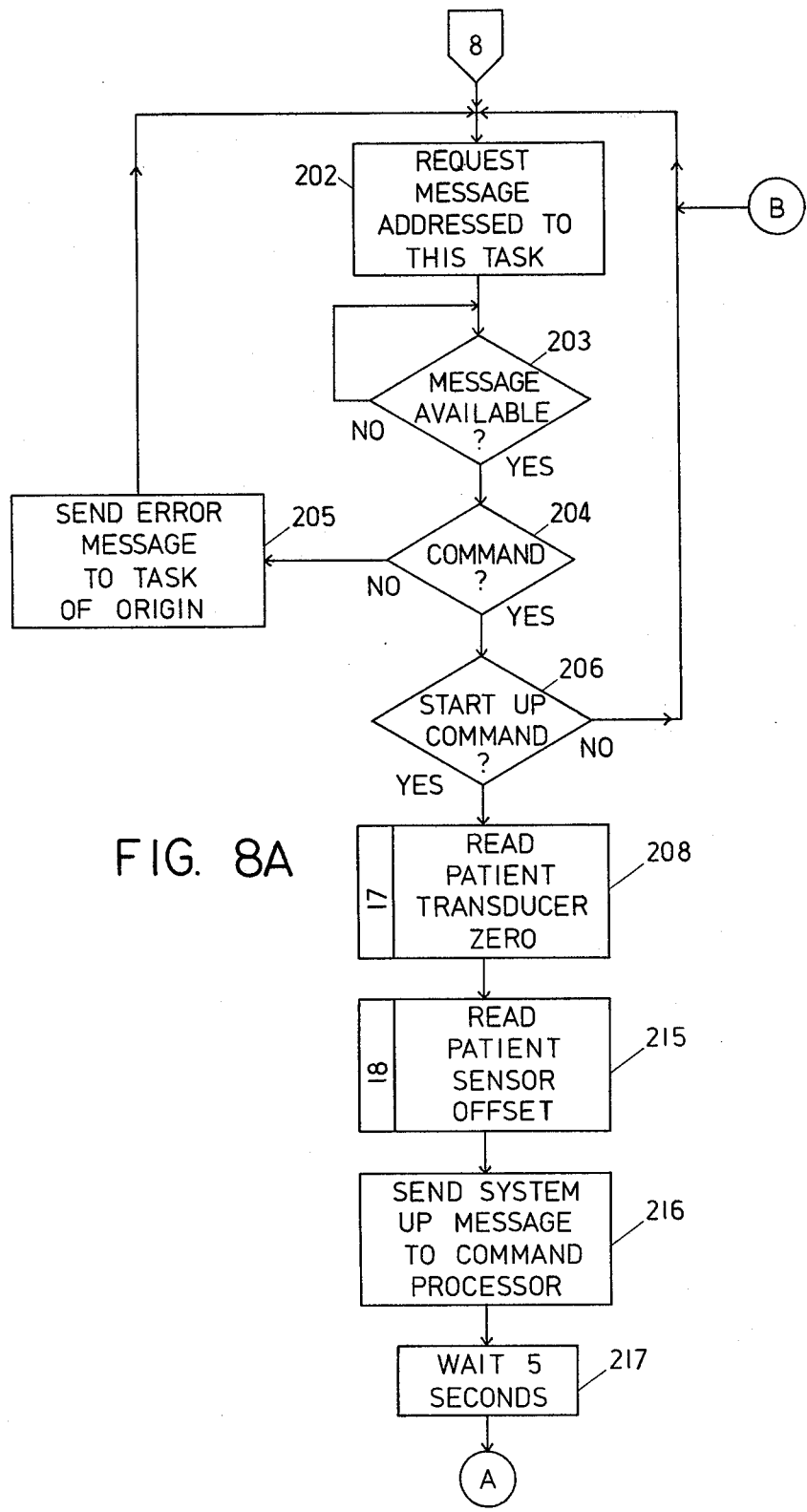

The leak task is shown in FIGS. 8A and B. Upon the initial assignment to this task by the scheduler, the leak task requests a message which may be addressed to the task (block 202), and checks to see if a message is available (block 203); if no message is available, the program cycles until a message does become available. When a message is received, it is determined whether the message is a command (block 204); if not, an error message is sent to the task which originated the message (block 205) and the program again requests a message addressed to the leak task (block 202). If a command message is received, it is checked to see if it is a start up command (block 206); if not, the program returns to block 202 and requests a message addressed to the leak task. If the start up command message is received, program proceeds to read the patient transducer zero (block 208) in subroutine 17, FIG. 17.

Figure 17:
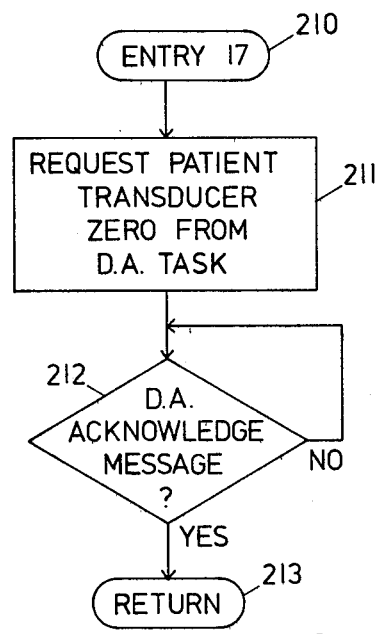

Referring to FIG. 17, after entry into subroutine 17 (block 210), a request is made for the patient transducer zero from the data acquisition task (block 211) and the program waits until the data acquisition task acknowledges the message (block 212); upon acknowledgment, return is made (block 213) to the leak task subroutine at block 208.

Figure 18:
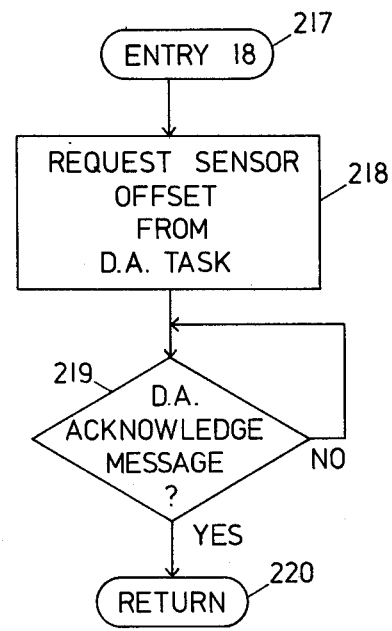
Figure 19:
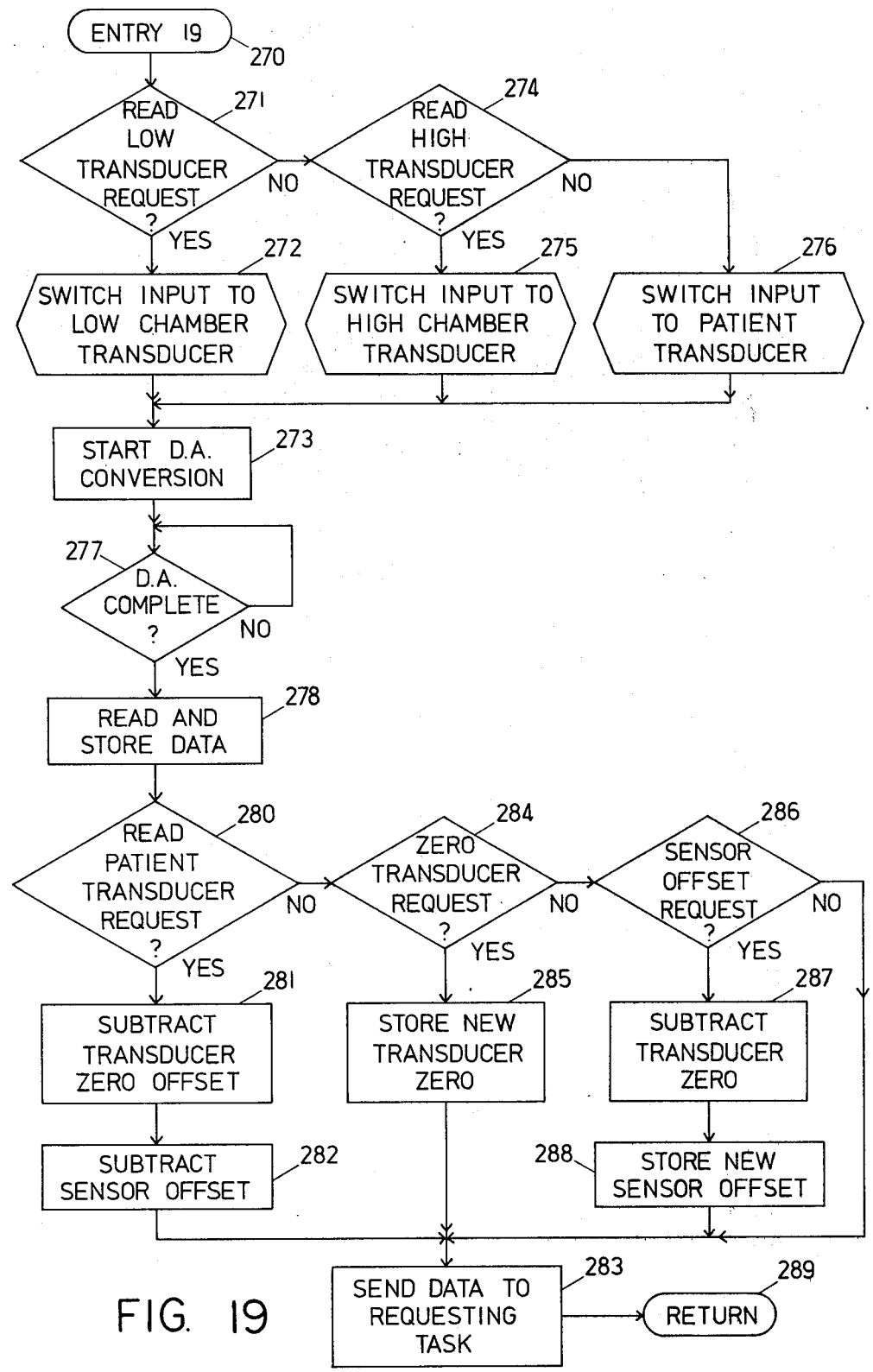

After the patient transducer zero has been read, the patient sensor offset is then determined (block 215) in subroutine 18, FIG. 18.

Referring to FIG. 18, after enter into the subroutine (block 217), the sensor offset is requested from the data acquisition task (block 218), and the program waits for the data acquisition task to acknowledge the message (block 219); upon acknowledgment of the message, return is made (block 220) to the leak task program at block 215.

After the patient transducer zero and patient sensor offset readings have been obtained, a system up message is sent to the command processor (block 216) and the program then waits for five seconds before any further readings are taken (block 217). It is noted that the foregoing steps in the leak task are performed during the initial start up of the system. In particular, at this time the pressure sensor 21 is being tested outside the body of a patient in ambient air to determine the patient sensor offset readings and the patient transducer zero readings under normal atmospheric conditions to establish a base line which can then be used to determine the actual pressure within a patient after the sensor 21 has been implanted. The five second waiting period allows all of the pressures within the chambers 20 and 24 and throughout the rest of the system to stablize.

Figure 8B:
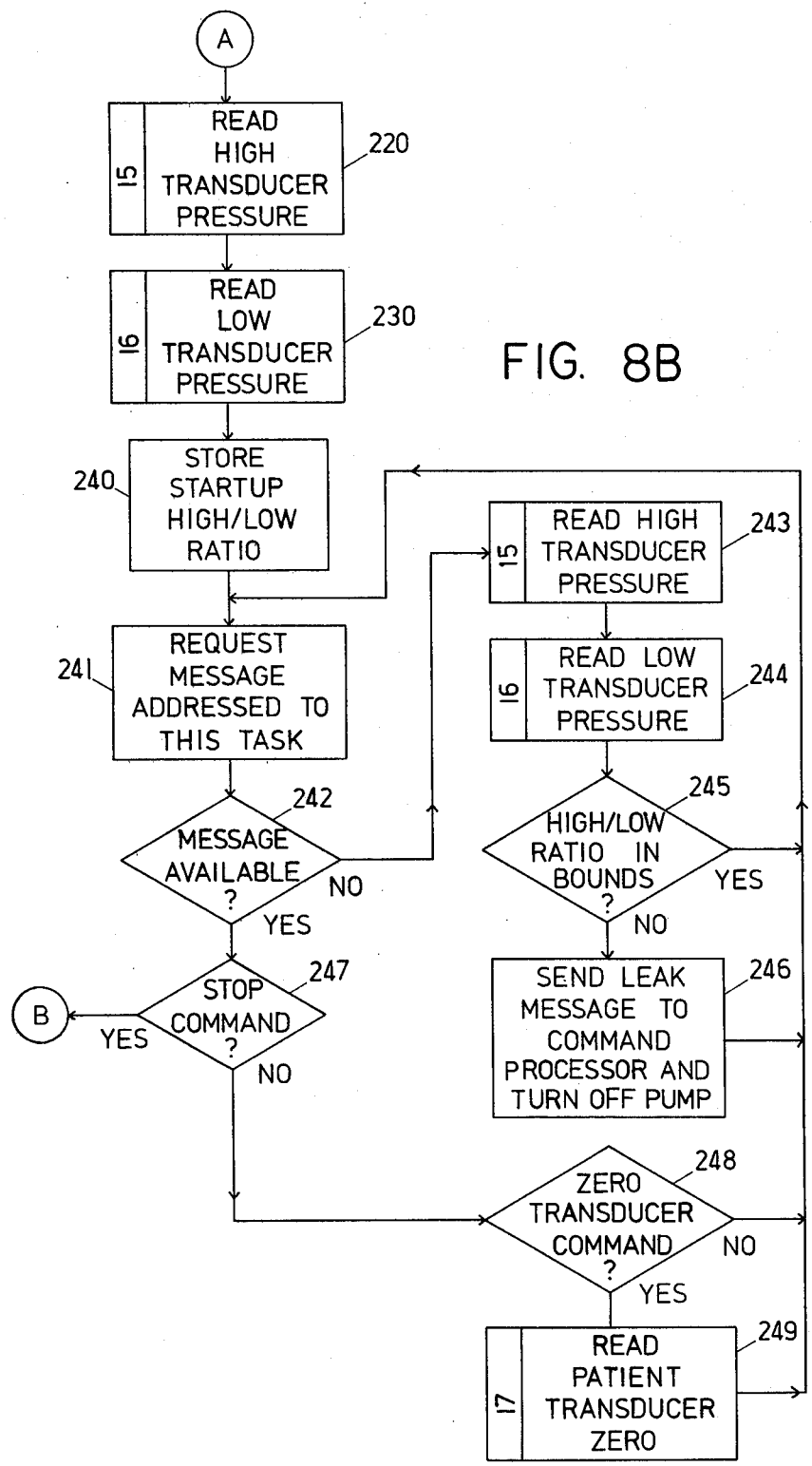
Figure 15:
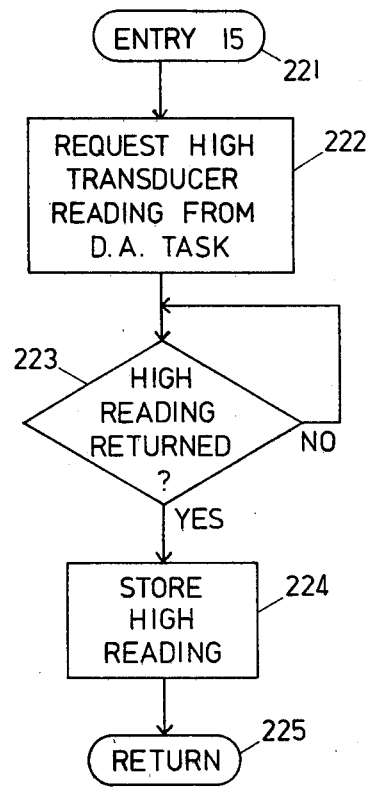

After the five second hold period has elapsed, the high pressure transducer is then read (block 220), FIG. 8B, in subroutine 15, shown in FIG. 15. After entry into this subroutine (block 221) a reading of the high pressure transducer is requested from the data acquisition task (222) and the program waits until the high pressure reading is returned (block 223). This high pressure transducer reading is then stored (block 224) and the program returns (block 225) to the leak task at block 270.

Figure 16:
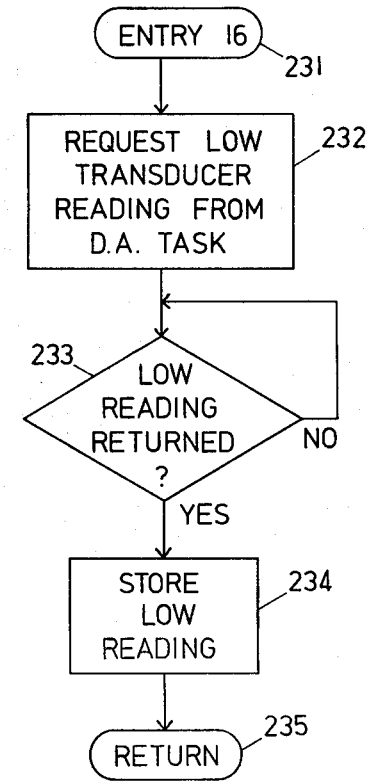

The leak task then proceeds to read the low pressure transducer (block 230), by performing subroutine 16, shown in FIG. 16. After entry into the subroutine (block 231), the low transducer reading is requested from the data acquisition task (block 232), and the program waits until the low pressure transducer reading is returned (block 233). When this reading is received, it is stored (block 234), and the program returns (block 235) to the leak task at block 230.

The initial high/low pressure transducer ratio is then calculated and stored (block 240) and a request is made for a message addressed to the leak task (block 241). The leak task is now in its active monitoring made in which it will continue to monitor the pressures within the high and low pressure chambers to determine if a leak occurs. This is done continuously while the pressure sensor is being inserted in the patient and, of course, after insertion.

If no message is available to the leak task (block 242) the high pressure transducer is then read (block 243) in subroutine 15. After reading the high pressure transducer, the low pressure transducer is read (block 244) in subroutine 16. The ratio of the high and low pressures is then calculated and compared to the initial start up high/low pressure transducer ratio (block 245). If no leaks in the system have occurred, the latest ratio should be identical or essentially identical to the initial high/low ratio. In the present program it has been found convenient to express the high and low pressure transducer readings as fixed point binary numbers, resulting in a fixed point quotient for the high/low ratio. The binary quotients so obtained from the initial high/low ratio and the latest high/low ratio are compared and the latest ratio is considered to be within bounds if it is the same as the initial high/low ratio or differs from the initial high/low ratio by no more than the least significant bit. For the system pressures described above with a resulting flow through the sensor of about 40 cubic centimeters (cc) per minute, a one bit difference in the ratios will correspond to a leakage rate of less than 3 cc per minute, so that leaks of 3 cc per minute or more will be detected. Greater accuracy and lower leak rates may be detected simply by utilizing floating point division and choosing a bit difference which corresponds to a desired maximum tolerable leakage flow rate.

If the high/low ratio is out of bounds, a leak message is sent to the command processor and the pump is turned off (block 246). The program returns to block 241 and requests a message addressed to the task.

If the high/low ratio is within bounds, the program recycles back to block 241 and requests a message addressed to the task and repeats the cycle. If the message at block 242 is available, the message is checked to see if it is a stop command (block 247), and if so, the program returns to the beginning of the leak task (FIG. 8A) and waits for a message (blocks 202 and 203). If no stop command is received, the leak task checks to see if a zero transducer command has been received (block 248); and, if not, the program recycles back to block 241 and requests a message addressed to the task. If the zero transducer command is received, the patient transducer zero is read (block 249) is subroutine 17, shown in FIG. 17. It may be desirable to periodically read the patient transducer zero level with the pressure sensor 11 placed within the patient, and the zero transducer command from the keyboard causes this to be done. After the patient transducer zero has been so read, the leak task returns to block 241 and continues to cycle and will do so until a stop command is received.

Figure 9:
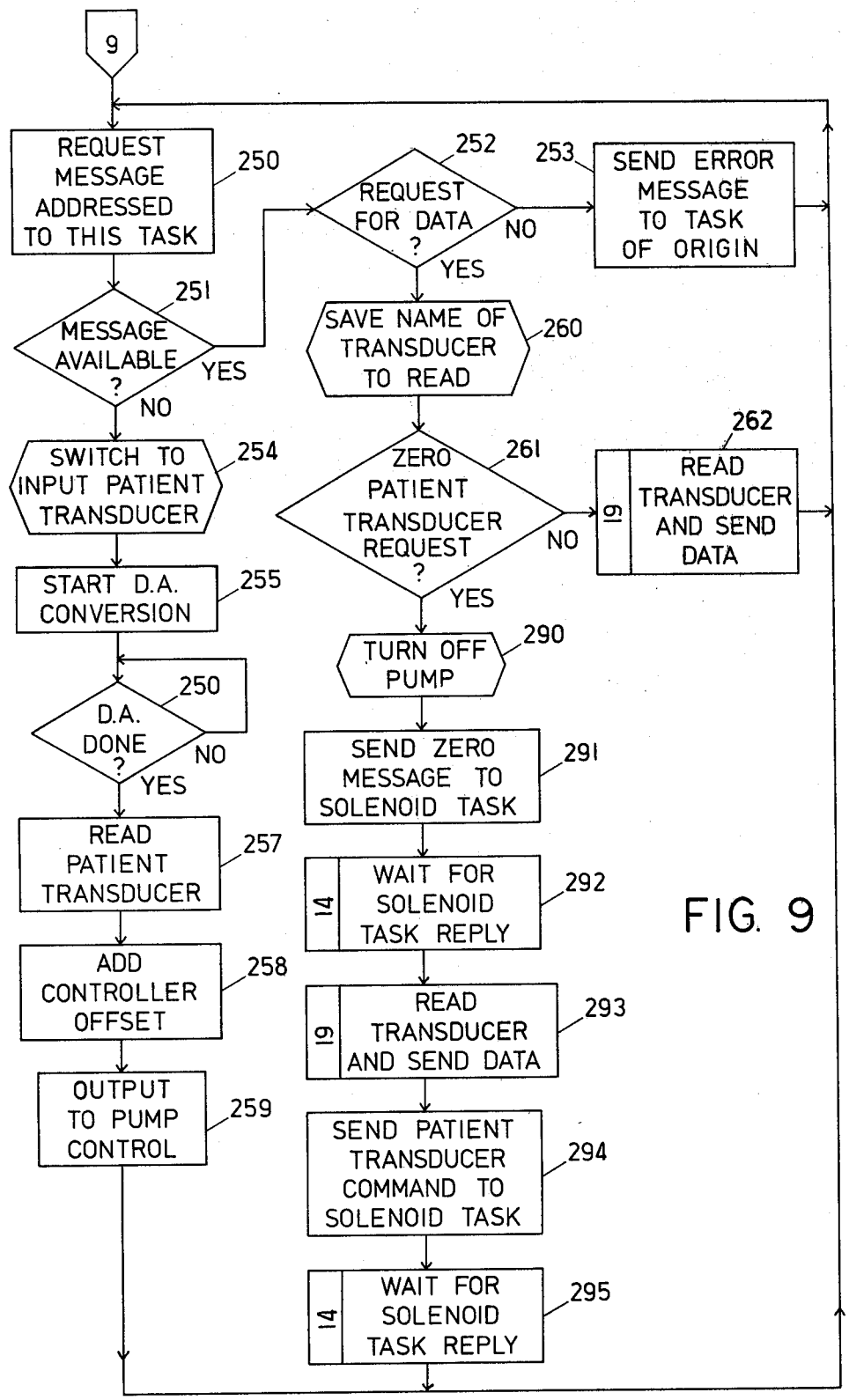

The data acquisition task, shown in FIG. 9, begins initially by requesting a message addressed to the task (block 250), checking to see if a message is available (block 251), and, if so, checking to see if it is a request for data (block 252). Only a request for data is a proper message for the data acquisition task, so that if a message other than a request for data is received, an error message is sent to the task originating the message (block 253), and return is made to block 250 to again request a message.

If no message is available at block 251, the program switches the analog to digital converter 56 to input the patient transducer (block 254), commands the start of the analog to digital conversion (block 225), and waits until the analog to digital conversion is done (block 256). After the analog to digital conversion is completed, the patient transducer level obtained by the analog to digital converter is read in (block 257), a pump controller offset amount is added to it (block 258), and the sum is provided to the pump controller through the digital to analog converter 73 (block 259). An initial controller offset is required to provide a minimum voltage level to the pump 17 through the proportional pump controller 74 since the pump will not operate below a minimum voltage level. The controller offset is adjusted to provide this minimum level. After the output is provided to the pump controller (block 259), the program recycles back to block 250 to check for a request addressed to the data acquisition task.

If a message is available at block 251 and if it is a request for data as determined at block 252, the program saves the name of the transducer which is to be read (block 260) and checks to see if it is a zero patient transducer request (block 261). If not, it must be a request to read the patient transducer, and therefore the patient transducer is read and the data is sent to the task which requested it (block 262) by performing subroutine 19. After subroutine 19 is completed, the program recycles back to block 250 to check for requests addressed to the data acquisition task.

Subroutine 19, shown in FIG. 19, after entry at block 270, determines whether the request is a request to read the low pressure chamber transducer 27 (block 271), and, if so, it switches the input of the analog to digital converter 56 to the low pressure chamber transducer (block 272) and starts the analog to digital conversion (block 273). If at block 271, a request to read the low pressure transducer is not received, it is then determined if a high pressure chamber transducer 26 reading request is received (block 274), and, if so, the analog to digital converter 56 is switched to the high pressure chamber transducer (block 275), and begins the analog to digital conversion (block 273). If a high transducer request has not been received, it must be a request to read the patient transducer 25 and the converter 56 is switched to the patient transducer (block 276), and the analog to digital conversion is started. The program checks to determine when the analog to digital conversion is complete (block 277), and then reads and stores the data from the converter (block 278).

After the data has been read and stored at block 278, a check is made to see if the request was a read patient transducer request (block 280); if so, the transducer zero offset is subtracted from the patient transducer reading (block 281) and the sensor offset is substracted from the difference previously calculated (block 282) and the data is sent back to the requesting task (block 283). If a patient transducer request was not received, it is next determined if a zero transducer request was received (block 284). If so, the new patient transducer zero reading is stored (block 285) and the data on the new transducer zero reading is sent back to the requesting task at block 283. If a zero transducer request had not been made, a check is made to determine if a sensor offset request was received (block 286), and, if so, the transducer zero reading is subtracted from the sensor offset reading (block 287) and the difference is stored as the new sensor offset (block 288) and the sensor data offset is sent back to the requesting task. If a sensor offset request had not been received as determined at block 286, then the request must have been for reading the low or high transducer, and this data is sent directly back to the requesting task at 283. After the data has been sent to the requesting task, return is made (block 289) back to the data acquisition task (FIG. 9) at block 262.

If a determination is made at block 261 that a zero patient transducer request has been received, the pump is turned off (block 290) by turning off the offset voltage provided through the D/A converter 63, and a zero message is sent to the solenoid valve control task (block 291). The program then waits for a reply from the solenoid control task (block 292) by performing subroutine 14. After reply is received from the solenoid task, the zero patient transducer is read (block 293) by performing subroutine 19 and the data is sent back to the task which has requested the patient transducer zero. The patient transducer command is then sent to the solenoid control task (block 294) and a wait is made for the solenoid task reply (block 295) by performing subroutine 14. After the reply from the solenoid task, the program recycles back to block 250 to check for a message addressed to the data acquisition task.

Figure 10:
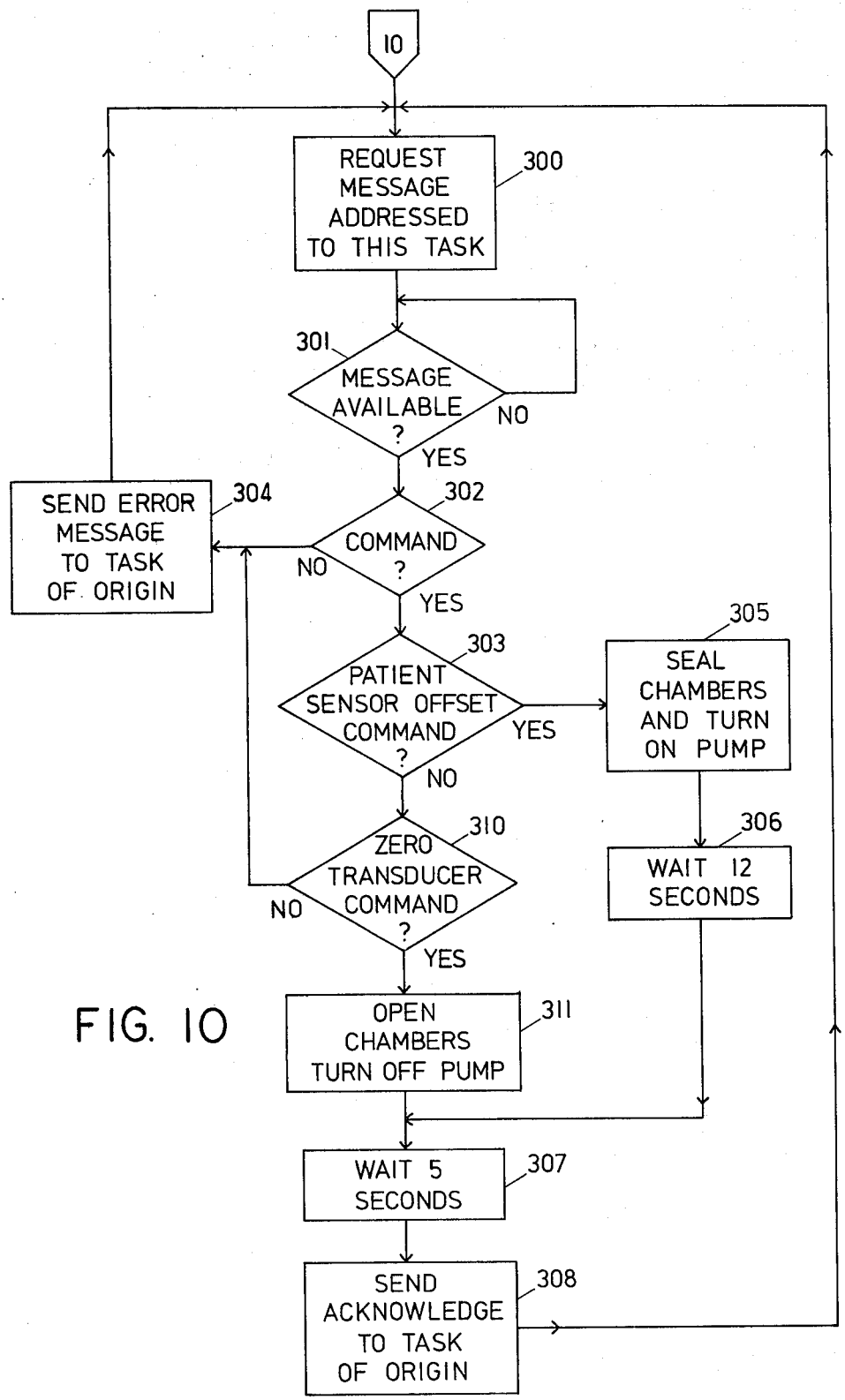

The solenoid control task is shown in FIG. 10. Initial entry into this task begins with a request for a message addressed to the task (block 300), and the program waits until the message is available (block 301). When the message becomes available, it is checked to see if it is a command (block 302), and if not, an error message is sent to the task originating the message (block 304) and the program returns to block 300 to request a message addressed to the task.

If a command is found at block 302, it is checked to see if it is a patient sensor offset command (block 303), and, if so, commands are sent through the output port 68 to turn off the solenoids 40 and 41 to seal the chambers, and a command is sent through the digital to analog converter 63 to the pump controller to turn on the pump (block 305). The program then waits 12 seconds to allow the pump to begin operating and pressurize the chambers (block 306), waits another 5 seconds (block 307) to allow the system to completely stablize, and then sends an acknowledgment of the command to the task of origin (block 308) indicating that the system is up and running and is ready to be tested for patient sensor offset. The program then waits at block 300 and 301 for another message addressed to the task.

If no patient sensor offset command was received at block 304, a check is then made to see if a zero transducer command was received (block 310); and, if not, return is made through block 304, sending an error message to the task that had originated the command, and the program proceeds back to block 300 to wait for another message addressed to the task. If the zero transducer command was received, the program then provides an output signal through the output port 68 to the solenoids 40 and 41 to open up the valves controlled by the solenoids and also provides an output through the converter 73 to the pump controller 74 to turn off the pump (block 311). The program then waits 5 seconds at block 307, and thereafter sends an acknowledgment of the receipt of the command to the task of origin and proceeds back to block 300 to wait for another message addressed to the solenoid control task. After the chambers are opened up and the pump is turned off, all of the chambers and the entire system should settle down to ambient pressure so that any of the pressure transducers can be read to determine their level under ambient air conditions.

Figure 20:
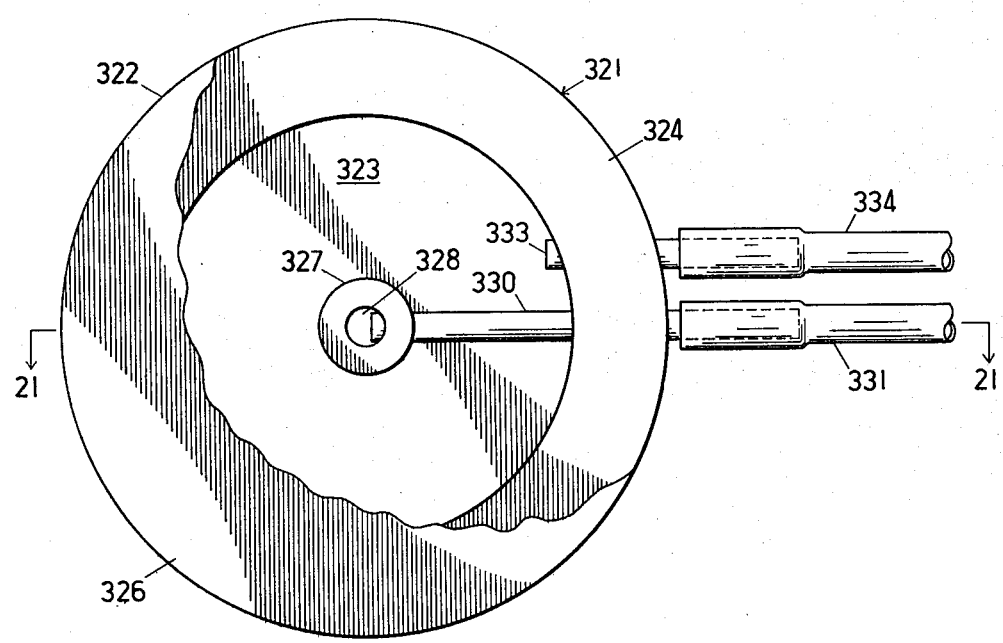
FIG. 20 is a bottom view of an embodiment of a pressure sensor adapted for implanting within a human patient, a portion thereof being broken away for illustration.
Figure 21:
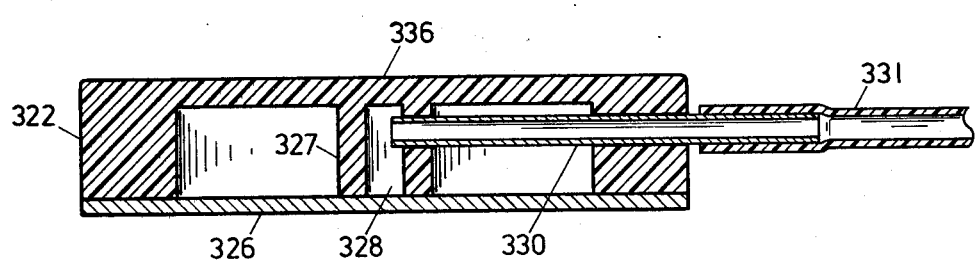
FIG. 21 is a cross-sectional view of the pressure sensor of FIG. 20 taken along the lines 21—21 of FIG. 20.

A particular embodiment of a pressure sensor which can act as the load in the system of FIG. 1 is shown generally at 321 in FIG. 20. The pressure sensor 321 includes a cup-shaped housing 322 formed as a circular disc of plastic having a circular open mouth 323 formed in one surface thereof surrounded by a peripheral annular face 324. A flexible diaphragm 326 is secured by glue or other adhesive or by sonic welding, as desired, to the peripheral face 324 of the housing to define a plenum in the mouth 323 under the diaphragm. A portion of the diaphragm 326 is shown broken away in FIG. 20 to illustrate the structure of the pressure sensor under the diaphragm. This structure includes a circular exhaust tube 327 centrally mounted in the mouth 323 and terminating—at a position adjacent the inner side of the diaphragm 326—in an annular face which surrounds the open bore 328 of the exhaust tube. As shown in FIG. 21, the annular face of the exhaust tube is formed substantially coplanar with the peripheral face 324 of the housing. A thin walled metal outlet pipe 330 has its inner bore in communication with the bore 328 of the exhaust tube and extends outwardly through the outer wall of the housing 322 and is connected to plastic tubing 331 corresponding to the return line 23 shown in FIG. 1. An inlet pipe 333, also formed of a thin walled metal pipe, extends through the outer wall of the housing 322 such that its bore is in communication with the plenum 323, with the outer end of the inlet pipe 333 being connected to plastic tubing 334 corresponding to the supply line 22 of FIG. 1. The outlet pipe 330 and the inlet pipe 333 are preferably mounted closely adjacent to one another at approximately the same elevation in the outer wall of the housing 322 to minimize the space taken up by the pipes and by the tubing connected to them.

As best shown in FIG. 21, the outlet pipe 330 passes through the plenum 323 and the wall of the exhaust tube 327 to the bore 328 of the exhaust tube. As is illustrated in FIG. 21, the top wall 336 of the sensor 321 need only be thick enough to provide structural strength and integrity. For example, the height of the pressure sensor 321, i.e., the distance from the outer surface of the diaphragm 326 to the surface of the top wall 336 of the housing, may be in the range of 1.5 mm., to thereby minimize the space within the patient that is occupied by the sensor. The structure of the sensor 321 also has the advantage of allowing the plastic tubes 331 and 334 to extend from the sensor in closely spaced, parallel relation. The inlet and outlet pipes 333 and 330 are preferably located at a position in the wall of the sensor housing above the bottom of the mouth of the housing such that the top wall of the sensor housing can be made as thin as desired.

The housing of the pressure sensor 321 is preferably formed of biocompatible plastic material such as silicone or polyurethane, and similar materials are used for the diaphragm 326 and tubing 331 and 334. A stiffer diaphragm (less elastic) may be provided, if desired, by molding a nylon mesh within the material of the diaphragm.

In operation, the diaphragm 326 closes off the bore 328 of the exhaust tube until the pressure inside the plenum, and thus in the line 334, is slightly greater than the pressure outside the sensor; at this pressure, the diaphragm is moved out to uncover the bore 328 and allow air to escape through the exhaust tube 330 and return line 331. Release of the air pressure within the plenum allows the diaphragm to move back and close the bore until sufficient pressure builds up to move the diaphragm away again. The pressure within the line 334 (corresponding to the line 12 of FIG. 1) thus fluctuates slightly but rapidly about the value of the pressure outside the sensor.

It is understood that the invention is not confined to the particular embodiments herein illustrated and described, but embraces such modified forms thereof as come within the scope of the following claims.

What is claimed is:

1. In a closed circulating gas system having a pump which draws gas at an inlet from a return line and delivers gas under pressure at an outlet to a supply line, and also having a load device which receives gas from the supply line and delivers it to the return line, apparatus for detecting leaks in the system comprising:
   (a) a first accumulator chamber connected in the supply line;
   (b) a second accumulator chamber connected in the return line;
   (c) first pressure transducer means for measuring the pressure in the first accumulator chamber and providing an output signal indicative thereof;
   (d) second pressure transducer means for measuring the pressure in the second accumulator chamber and providing an output signal indicative thereof;
   (e) control means responsive to the output signals of the first and second pressure transducer means for comparing the pressure measured in the first accumulator chamber with the pressure measured in the second accumulator chamber and providing a leak warning output signal if the compared pressures change with respect to one another in excess of a selected range, thereby indicating that the flow through the two accumulator chambers is not equal and a leak in the system has occured;

(f) a load device comprising a pressure sensor connected between the supply and return lines which includes:
  (1) a cup-shaped housing having an open mouth and having an inlet and an outlet formed therein;
  (2) a flexible diaphragm sealed over the open mouth of the housing to define a plenum between the walls of the mouth in the housing and the diaphragm, and wherein the inlet formed in the housing is in communication with the plenum;
  (3) an exhaust tube centrally mounted in the housing within the plenum with an end thereof terminating adjacent the inner side of the diaphragm and connected to be in communication with the outlet from the housing, the supply line being connected to the inlet to the housing and the return line being connected to the outlet from the housing;

(g) a flow restrictor connected in the supply line between the first accumulator chamber and the pressure sensor;

(h) load pressure transducer means for measuring the pressure in the supply line between the restrictor and the pressure sensor and providing an output signal indicative thereof which is supplied to the control means; and (i) the control means also providing a display to an operator of the pressure measured by the load pressure transducer means.

2. The system of claim 1 including a bypass valve connected around the pump and responsive to the leak warning signal from the control means, the bypass valve being operative to open when the leak warning signal is received to shunt the outlet of the pump back to its inlet and to relieve pressure within the system including equalizing the pressures within the first and second accumulator chambers.

3. The system of claim 2 including a pressure release valve connected to the return line, the pressure release valve being responsive to a signal from the control means to open at the same time that the bypass valve opens and to place the return line in communication with the ambient atmosphere.

4. The system of claim 1 wherein the volume of the second chamber is substantially greater than the volume of the first chamber.

5. The system of claim 1 wherein the control means also provides an audio signal when the pressure measured by the load pressure transducer means exceeds a selected high pressure or is below a selected low pressure.

6. The system of claim 1 wherein the pump is responsive to an input signal to vary the displacement of the pump in direct relation to the input signal, and wherein the control means varies the input signal to the pump in proportion to the output pressure measured by the sensor pressure transducer means so as to control the displacement of the pump in direct relation to the pressure at the pressure sensor.

7. The system of claim 1 including means for converting the output signals of the first and second pressure transducer means to digital data signals, and wherein the control means compares the digital pressure signals from the first and second transducer means by periodically dividing one of the digitized output signals into the other to provide an initial digital ratio which is stored and a latest ratio, the control means comparing the latest ratio with the initial ratio and providing a leak warning output signal if the latest ratio deviates from the initial ratio in excess of a selected tolerance amount.

8. The system of claim 7 wherein the ratios of the transducer means output signals are provided in fixed point binary digital form and the leak warning output signal is provided if the latest ratio differs from the initial ratio by more than the least significant bit.

9. The system of claim 1 wherein the pump is responsive to an input signal to vary the displacement of the pump in direct relation to the input signal, and wherein the control means varies the input signal to the pump in proportion to the difference between the load pressure transducer means signal and the first pressure transducer means signal to control the pump so that the flow rate through the restrictor is maintained substantially constant.

10. Pressure monitoring apparatus comprising:
(a) a pump which draws gas in at an inlet and delivers gas under pressure at an outlet;
(b) a pressure sensor including:
  (1) a cup shaped housing having an open mouth and having an inlet and outlet formed therein;
  (2) a flexible diaphragm sealed over the open mouth of the housing to define a plenum between the walls of the mouth in the housing and the diaphragm, and wherein the inlet formed within the housing is in communication with the plenum;
  (3) an exhaust tube centrally mounted in the housing within the plenum with an end thereof terminating adjacent the inner side of the diaphram and connected to be in communication with the outlet from the housing;
(c) a supply line connected from the outlet of the pump to the inlet in the sensor housing to supply gas under pressure to the sensor and a return line connected from the outlet in the sensor housing to the inlet of the pump;
(d) a first accumulator chamber connected in the supply line;
(e) a second accumulator chamber connected in the return line;
(f) a flow restrictor connected in the supply line between the first accumulator chamber and the inlet to the pressure sensor housing;
(g) load pressure transducer means for measuring the pressure in the supply line between the restrictor and the pressure sensor and providing an output signal indicative thereof, whereby changes in ambient pressure at the pressure sensor will result in movement of the diaphragm to alternately open and close the exhaust tube to automatically maintain the pressure within the plenum approximately equal to the ambient pressure, and whereby the load pressure transducer means will measure a pressure which is approximately equal to the pressure surrounding the sensor including pressures lower than the ambient atmospheric pressure which are no lower than the pressure within the second accumulator chamber.

11. The apparatus of claim 10 wherein the pump is responsive to an input signal to vary the displacement of the pump in direct relation to the input signal, and including control means responsive to the signal from the load pressure transducer means so as to control the displacement of the pump in direct relation to the pressure at the pressure sensor.

12. The apparatus of claim 10 including:
   (1) first pressure transducer means for measuring the pressure in the first accumulator chamber and providing an output signal indicative thereof;
   (2) second pressure transducer means for measuring the pressure in the second accumulator chamber and providing an output signal indicative thereof; and
   (3) control means responsive to the output signals of the first and second pressure transducer means for comparing the pressure measured in the first accumulator chamber with the pressure measured in the second accumulator chamber and providing a leak warning output signal if the compared pressures change with respect to one another in excess of a selected range, thereby indicating that the flow through the two accumulator chambers is not equal and a leak has occurred.

13. The apparatus of claim 12 wherein the pump is responsive to an input signal to vary the displacement of the pump in direct relation to the input signal, and including control means responsive to the signals from the load pressure transducer means and the first pressure transducer means for varying the input signal to the pump in proportion to the difference between the load pressure transducer means signal and the first transducer means signal to maintain the flow rate through the restrictor substantially constant.

14. The apparatus of claim 12 including a bypass valve connected around the pump and responsive to the leak warning signal from the control means, the bypass valve being operative to open when the leak warning signal is received to shunt the outlet of the pump back to its inlet and to relieve pressure within the system including equalizing the pressures within the first and second accumulator chambers.

15. The apparatus of claim 14 including a pressure release valve connected to the return line, the pressure release valve being responsive to the signal from the control means to open at the same time that the bypass valve opens and to place the return line in communication with the ambient atmosphere.

16. The apparatus of claim 12 wherein the volume of the second chamber is substantially greater than the volume of the first chamber.

17. The apparatus of claim 12 wherein the control means is responsive to the output signal from the load pressure transducer means and provides a display to an operator of the pressure measured by the load pressure transducer means, and wherein the control means also provides an audio output signal when the pressure measured by the sensor pressure transducer means exceeds a selected high pressure or is below a selected low pressure.

18. The apparatus of claim 12 including means for converting the output signals of the first and second pressure transducer means to digital data signals, and wherein the control means compares the digital pressure signals from the first and second transducer means by periodically dividing one of the digitized output signals into the other to provide an initial digital ratio which is stored and a latest ratio, the control means comparing the latest ratio with the initial ratio and providing a leak warning output signal if the latest ratio deviates from the initial ratio in excess of a selected tolerance amount.

19. The apparatus of claim 18 wherein the ratios of the transducer means output signals are provided in fixed point binary digital form and the leak warning output signal is provided if the latest ratio differs from the initial ratio by more than the least significant bit.

20. The apparatus of claim 18 wherein the control means includes a microprocessor which periodically calculates the ratios of the output signals of the first and second pressure transducer means and provides the leak warning signal if the deviation from the initial ratio is in excess of the selected tolerance amount.

21. In a closed circulating gas system having a pump which draws gas at an inlet from a return line and delivers gas under pressure at an outlet to a supply line, and also having a load device which receives gas from the supply line and delivers it to the return line, apparatus for detecting leaks in the system comprising:
   (a) a first accumulator chamber connected in the supply line;
   (b) a second accumulator chamber connected in the return line;
   (c) first pressure transducer means for measuring the pressure in the first accumulator chamber and providing an output signal indicative thereof;
   (d) second pressure transducer means for measuring the pressure in the second accumulator chamber and providing an output signal indicative thereof;
   (e) control means responsive to the output signals of the first and second pressure transducer means for comparing the pressure measured in the first accumulator chamber with the pressure measured in the second accumulator chamber and providing a leak warning output signal if the compared pressure change with respect to one another in excess of a selected range, thereby indicating that the flow through the two accumulator chambers is not equal and a leak in the system has occurred;
   (f) a bypass valve connected around the pump and responsive to the leak warning signal from the control means, the bypass valve being operative to open when the leak warning signal is received to shunt the outlet of the pump back to its inlet and to relieve pressure within the system including equalizing the pressures within the first and second accumulator chambers; and
   (g) a pressure release valve connected to the return line, the pressure release valve being responsive to a signal from the control means to open at the same time that the bypass valve opens and to place the return line in communication with the ambient atmosphere.

22. In a closed circulating gas system having a pump which draws gas at an inlet from a return line and delivers gas under presure at an outlet to a supply line, and also having a load device which receives gas from the supply line and delivers it to the return line, apparatus for detecting leaks in the system comprising:
   (a) a first accumulator chamber connected in the supply line;
   (b) a second accumulator chamber connected in the return line;

(c) first pressure transducer means for measuring the pressure in the first accumulator chamber and providing an output signal indicative thereof;

(d) second pressure transducer means for measuring the pressure in the second accumulator chamber and providing an output signal indicative thereof;

(e) control means responsive to the output signals of the first and second pressure transducer means for comparing the pressure measured in the first accumulator chamber with the pressure measured in the second accumulator chamber and providing a leak warning output signal if the compared pressures change with respect to one another in excess of a selected range, thereby indicating that the flow through the two accumulator chambers is not equal and a leak in the system has occurred; and (f) means for converting the output signals of the first and second pressure transducer means to digital data signals, and wherein the control means compares the digital pressure signals from the first and second transducer means by periodically dividing one of the digitized output signals into the other to provide an initial digital ratio which is stored and a latest ratio, the control means comparing the latest ratio with the initial ratio and providing a leak warning output signal if the latest ratio deviates from the initial ratio in excess of a selected tolerance amount.

23. The system of claim 22 wherein the control means includes a microprocessor which periodically calculates the ratios of the output signals of the first and second pressure transducer means and provides the leak warning signal if the deviation from the initial ratio is in excess of the selected tolerance amount.

* * * * *